(12) United States Patent
Backman et al.

(10) Patent No.: US 8,131,348 B2
(45) Date of Patent: **\*Mar. 6, 2012**

(54) SYSTEMS, METHODS AND APPARATUSES OF ELASTIC LIGHT SCATTERING SPECTROSCOPY AND LOW COHERENCE ENHANCED BACKSCATTERING SPECTROSCOPY

(75) Inventors: Vadim Backman, Chicago, IL (US); Hemant Roy, Highland Park, IL (US); Brand Randall, Highland Park, IL (US); Yang Liu, Somerset, NJ (US); Jeremy Rogers, Chicago, IL (US); Vladimir Turzhitsky, Evanston, IL (US)

(73) Assignees: Northshore University Healthsystem, Evanston, IL (US); Northwestern University, Evanston, IL (US)

( * ) Notice: Subject to any disclaimer, the term of this patent is extended or adjusted under 35 U.S.C. 154(b) by 901 days.

This patent is subject to a terminal disclaimer.

(21) Appl. No.: 11/803,418

(22) Filed: May 14, 2007

(65) Prior Publication Data

US 2009/0009759 A1 Jan. 8, 2009

Related U.S. Application Data

(60) Provisional application No. 60/799,970, filed on May 12, 2006, provisional application No. 60/801,954, filed on May 19, 2006.

(51) Int. Cl.
*A61B 6/00* (2006.01)
*G01J 3/40* (2006.01)

(52) U.S. Cl. .................................. 600/476; 356/303

(58) Field of Classification Search .............. 600/476; 356/303, 446, 497
See application file for complete search history.

(56) References Cited

U.S. PATENT DOCUMENTS

| | | | |
|---|---|---|---|
| 5,037,202 | A | 8/1991 | Batchelder et al. |
| 5,303,024 | A | 4/1994 | Thierman |
| 5,650,847 | A | 7/1997 | Maltsev et al. |
| 5,799,656 | A | 9/1998 | Alfano et al. |
| 6,320,660 | B1 | 11/2001 | Ju et al. |
| 6,405,070 | B1 | 6/2002 | Banerjee |
| 6,556,853 | B1 | 4/2003 | Cabib et al. |

(Continued)

OTHER PUBLICATIONS

Stephen B. Haley et al., "Wave propagation in one-dimensional disordered structures", The American Physical Society, Physical Review B, Apr. 15, 1992, pp. 8572-8584, vol. 45, No. 15.

(Continued)

*Primary Examiner* — Tse Chen
*Assistant Examiner* — Hien Nguyen
(74) *Attorney, Agent, or Firm* — Oliff & Berridge, PLC

(57) ABSTRACT

Systems, methods, and apparatuses of elastic light scattering spectroscopy and low-coherence enhanced backscattering spectroscopy are described here. An apparatus couple-able to a light source and a target object, to facilitate light transmission between the light source and the target object, the apparatus comprises: a probe to emit incident light that is partially coherent obtained from the light source onto the target object and to receive interacted light, the interacted light to be backscattered light from illumination of the incident light on the target object, the probe comprising: a delivery channel having at least one delivery optical fiber with a distal end portion couple-able to the light source and a proximal end portion suited to couple the incident light to the target object, a collection channel having a first collection optical fiber suited to collect substantially co-polarized backscattered light and a second collection optical fiber suited to collect substantially cross-polarized backscattered light.

56 Claims, 18 Drawing Sheets

U.S. PATENT DOCUMENTS

| | | | |
|---|---|---|---|
| 6,639,674 | B2 | 10/2003 | Sokolov et al. |
| 6,650,357 | B1 | 11/2003 | Richardson |
| 6,922,583 | B1 | 7/2005 | Perelman et al. |
| 6,927,860 | B2 | 8/2005 | Podoleanu et al. |
| 7,061,622 | B2 | 6/2006 | Rollins et al. |
| 7,652,772 | B2 * | 1/2010 | Backman et al. ............. 356/497 |
| 2003/0137669 | A1 * | 7/2003 | Rollins et al. ................. 356/479 |
| 2003/0215846 | A1 | 11/2003 | Watt et al. |
| 2004/0171567 | A1 | 9/2004 | Sidransky et al. |
| 2004/0189987 | A1 | 9/2004 | Bondurant et al. |
| 2004/0223162 | A1 | 11/2004 | Wax |
| 2005/0046821 | A1 | 3/2005 | Hanson et al. |
| 2005/0265586 | A1 | 12/2005 | Rowe et al. |
| 2006/0155195 | A1 | 7/2006 | Maier et al. |
| 2007/0078348 | A1 | 4/2007 | Holman |
| 2007/0201033 | A1 | 8/2007 | Desjardins et al. |

OTHER PUBLICATIONS

Irving Itzkan et al., "Confocal light absorption and scattering spectroscopic microscopy monitors organelles in live cells with no exogenous labels", Proceedings of the National Academy of Sciences, Oct. 30,2007, pp. 17255-17260, vol. 104, No. 44.

Kumar, N., "Resistance fluctuation in a one-dimensional conductor with static disorder", The American Physical Society, Physical Review B, Apr. 15, 1985, pp. 5513-5515, vol. 31, No. 8.

Hariharan Subramanian et al., "Nanoscale Cellular Changes in Field Carcinogenesis Detected by Partial Wave Spectroscopy", American Association for Cancer Research Journal, Jul. 1, 2009, pp. 5357-5363.

Hariharan Subramanian et al., "Optical methodology for detecting histologically unapparent nanoscale consequences of genetic alterations in biological cells", Proceedings of the National Academy of Sciences, Dec. 23, 2008, pp. 20124-20129, vol. 105, No. 51.

Hariharan Subramanian et al., "Partial-wave microscopic spectroscopy detects subwavelength refractive index fluctuations: an application to cancer diagnosis" Optics Letters, Optical Society of America, Feb. 15, 2009, pp. 518-520, vol. 34, No. 4.

Yang Liu et al., "Elastic backscattering spectroscopic microscopy", Optic Letters, Optical Society of America, Sep. 15, 2005, pp. 2445-2447, vol. 30, n. 18.

Young L. Kim et al., "Low-coherent backscattering spectroscopy for tissue characterization", Applied Optics, Jan. 20, 2005, pp. 366-377, vol. 44, No. 3.

Young L. Kim et al., "Coherent backscattering spectroscopy", Optics Letters, optical Society of American, Aug. 15, 2004, pp. 1906-1908, vol. 29, No. 16.

Young L. Kim et al., "Low-coherent enhanced backscattering: review of principles and applications for colon cancer screening", Journal of Biomedical Optics, Jul./Aug. 2006, pp. 041125-1-041125-10, vol. 11(4).

Young L. Kim et al., "Depth-resolved low-coherence enhanced backscattering", Optics Letters, Optical Society of America, Apr. 1, 2005, pp. 741-743, vol. 30, No. 7.

Adam Wax, et al., "Cellular Orgnaization and Substructure Measured Using Angle-Resolved Low-Coherence Interferometry", Biophysical Journal, Apr. 2002, pp. 2256-2264, vol. 82.

International Preliminary Report on Patentability dated Feb. 26, 2009 from PCT/US07/017894.

International Search Report and Written Opinion dated Mar. 19, 2008 from PCT/US07/017894.

Ingle, James D. et al., Spectrochemical Analysis, Prentice-Hall Inc., 1988, ISBN 0-13-826876-2 p. 520.

Ramanujam, Nirmala, Flourescence Spectrocopy of Neoplastic and Non-Neoplastic Tissues, Neoplasma, Neoplasma Press, Inc., Jan. 2000, V. 2(102), p. 89-117.

Brownson, RC et al., Family history of cancer and risk of lung cancer in lifetime non-smokers and long-term ex-smokers, Int J. Epidemiol, Apr. 1997, vol. 26, No. 2, p. 256-263 (abstract).

International Search Report and Written Opinion dated Jul. 22, 2008 from PCT/US07/11404.

International Preliminary Report on Patentability dated Nov. 17, 2008 from PCT/US07/11404.

Wolf, P.E., Maret, G., Akkermans, E. & Maynard, R., "Optical Coherent Backscattering by Random-Media—an Experimental-Study." Journal de Physique 49, 63-75 (1988).

Yoo, K. M., Tang, G.C., and Alfano, R.R., "Coherent Backscattering of Light from Biological Tissues." Applied Optics 29, 3237-3239 (1990).

Chen, L.C., Hao, C. Y., and Chiu, Y. C., et al., "Alteration of gene expression in normal-appearing colon mucosa of APCminmice and human cancer patients." Cancer Res 64, 3694-700 (2004).

Liu, Y., Kim, Y. L., Li, X., and Backman, V. Investigation of depth selectivity of polarization gating for tissue characterization. Opt. Express, 13: 601-611, 2005.

Roy, H. K., Kim, Y. L, Liu, Y., Wali, R. K, Goldberg, M. J., Turzhitsky, V., Horwitz, J., and Backman, V. "Risk stratification of colon carcinogenesis through enhanced backscattering (EBS) spectroscopy analysis of the uninvolved colonic mucosa," Clinical Cancer Research 12(3), 961-968 (2006).

Siegel, M. P., Kim, Y. L., Roy, H., Wali, R., and Backman, V. "Assessment of Blood Supply in Superficial Tissue using Polarization Gated Elastic Light Scattering Spectroscopy," Appl Optics, accepted 45(2), 335-342 (2006).

Wali, R. K., Roy, H. K., Kim, Y. L., Liu, Y., Koetsier, J. L, Kunte, D. P., Goldberg, M. J., Turzhitsky, V., and Backman, V. "Increased Microvascular Blood Content is an Early Event in Colon Carcinogenesis," Gut 54, 654-660 (2005).

Kim, Y., Liu, Y., Wali, R. K., Roy, H. K., Goldberg, M. J., Kromine, A. K., Chen, K., and Backman, V. "Simultaneous measurement of angular and spectral properties of light scattering for characterization of tissue microarchitecture and its alteration in early precancer," IEEE J. Sel. Top. Quantum Electron. 9, 243-257 (2003).

Kim, Y. L., Pradhan, P., Subramanian, H., Liu, Y., Kim, M. H., and Backman, V. "Origin of low-coherence enhanced backscattering," Optics Letters 31(10), 1459-1461 (2006).

Office Action from U.S. Appl. No. 11/891,877 dated Nov. 12, 2009.

* cited by examiner

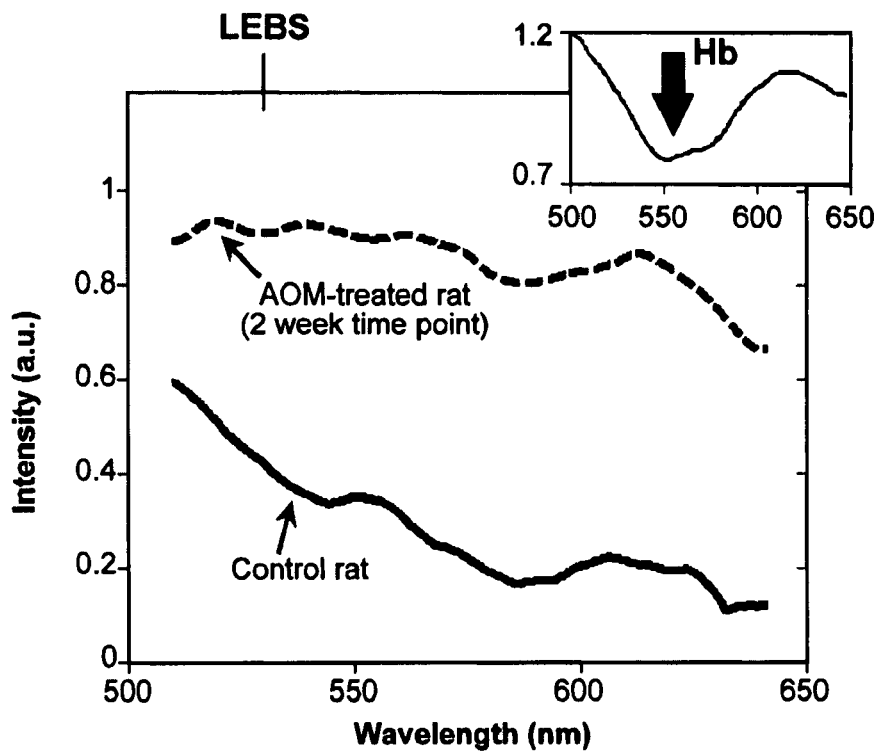
Figure 7A
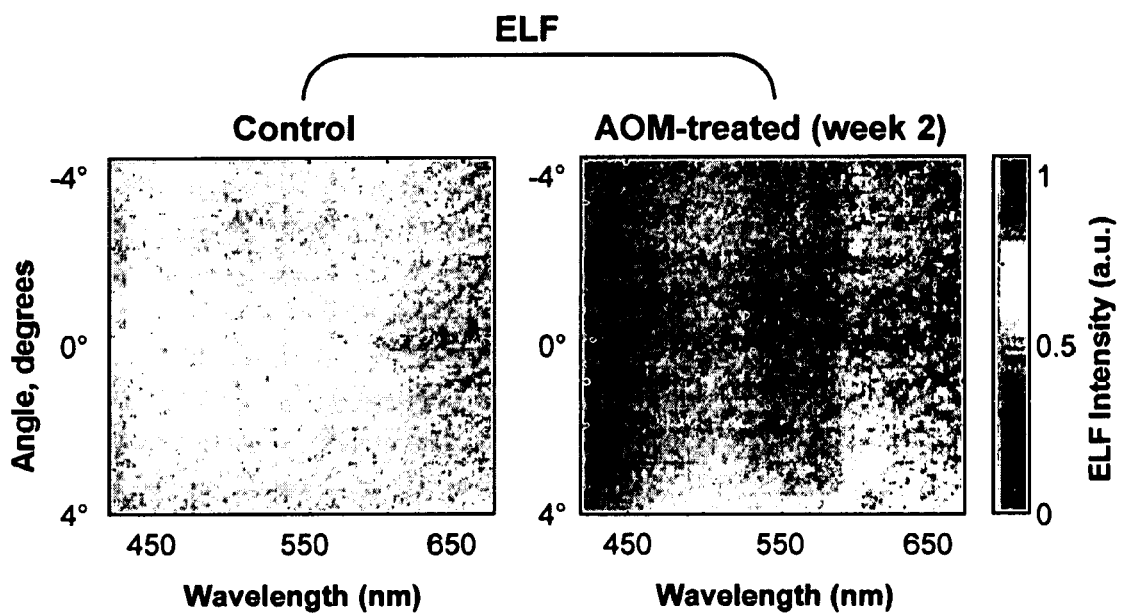
Figure 7B  Figure 7C

| Sensitivity | 95° |
|---|---|
| Specificity | 91° |
| Positive Predictive Value | 86° |
| Negative Predictive Value | 97° |

*Figure 10*

|  | 2 weeks after AOM treatment (pre-ACF stage) ||
|  | LEBS markers only | ELF and LEBS markers |
| --- | --- | --- |
| Sensitivity | 84° | 100° |
| Specificity | 72° | 100° |
| Positive Predictive Value | 78° | 100° |
| Negative Predictive Value | 79° | 100° |

*Figure 12*

| Rectal marker | Two factor ANOVA p-value for the effect of age | Correlation coefficient |
|---|---|---|
| ELF spectral slope | 0.91 | 0.04 |
| LEBS spectral slope | 0.59 | 0.02 |
| Correlation decay rate | 0.39 | -0.13 |
| LEBS enhancement | 0.51 | -0.05 |
| LEBS width | 0.73 | -0.01 |
| PCI | 0.52 | -0.03 |

*Figure 17*

SYSTEMS, METHODS AND APPARATUSES OF ELASTIC LIGHT SCATTERING SPECTROSCOPY AND LOW COHERENCE ENHANCED BACKSCATTERING SPECTROSCOPY

CLAIM OF PRIORITY

This application claims priority to U.S. Provisional Patent Applications Nos. 60/799,970, titled "LOW-COHERENCE ENHANCED BACKSCATTERING SPECTROSCOPY AND APPLICATIONS OF SAME", filed May 12, 2006, and 60/801,954, titled "FOUR-DIMENSIONAL ELASTIC LIGHT SCATTERING SPECTROSCOPY, LOW-COHERENCE ENHANCED BACKSCATTERING SPECTROSCOPY, RELATED OPTICAL MARKERS, AND APPLICATIONS OF SAME", which was filed on May 19, 2006, the contents of both of which are expressly incorporated by reference herein.

CROSS-REFERENCE TO RELATED PATENT APPLICATION

This application is related to a co-pending U.S. patent application entitled "MULTI-DIMENSIONAL ELASTIC LIGHT SCATTERING", filed 27 Oct. 2005 with the same assignee as the present disclosure. The applicants of that application are also applicants of this application. This application is also related to U.S. Provisional Patent Application entitled, "LOW-COHERENCE ENHANCED BACKSCATTERING SPECTROSCOPY AND APPLICATIONS OF SAME," filed 12 May 2006. The disclosures of the above-identified co-pending applications are incorporated in their entirety herein by reference.

This application is related to a copending U.S. patent application Ser. No. 11/604,653, entitled "METHOD OF RECOGNIZING ABNORMAL TISSUE USING THE DETECTION OF EARLY INCREASE IN MICROVASCULAR BLOOD CONTENT", filed 27 Nov. 2005 with the same assignee as the present disclosure claiming priority to U.S. Application No. 60/801,947 entitled "GUIDE-TO-COLONOSCOPY BY OPTICAL DETECTION OF COLONIC MICRO-CIRCULATION AND APPLICATIONS OF THE SAME", filed 19 May 2006. The applicants of the above applications are also applicants of this application. The disclosure of the above identified copending applications is incorporated in its entirety herein by reference.

This application is further related to a copending U.S. patent application Ser. No. 11/604,659, entitled "APPARATUS FOR RECOGNIZING ABNORMAL TISSUE USING THE DETECTION OF EARLY INCREASE IN MICROVASCULAR BLOOD CONTENT", filed 27 Nov. 2005 with the same assignee as the present disclosure claiming priority to U.S. Application No. 60/801,947 entitled "GUIDE-TO-COLONOSCOPY BY OPTICAL DETECTION OF COLONIC MICRO-CIRCULATION AND APPLICATIONS OF THE SAME", filed 19 May 2006. The applicants of the above applications are also applicants of this application. The disclosure of the above identified copending applications is incorporated in its entirety herein by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference. In terms of notation, hereinafter, a superscript "[″]" represents the nth reference cited in the reference list. For example, [24] represents the 24th reference cited in the reference list, namely, Backman, V. et al. Detection of preinvasive cancer cells. Nature 406, 35-36 (2000).

FEDERALLY-SPONSORED RESEARCH

This invention was made with government support under Grant Nos. BES-0547480 awarded by the National Science Foundation and Grant No. U01 CA111257 and Grant No R21CA102750 awarded by the National Institutes of Health. The government has certain rights in the invention.

TECHNICAL FIELD

The present disclosure relates generally to light scattering, and in particular to low-coherence enhanced backscattering spectroscopy, elastic light scattering spectroscopy and/or applications of light scattering including medical diagnostic and treatment purposes.

BACKGROUND

Pancreatic cancer is one of the leading causes of cancer death in the United States and has the worst prognoses of major cancers as illustrated by almost the same incidence (32,800) and mortality (31,800) rates and an overall 5-year survival rate <5%. The reason for this grim prognosis is that most pancreatic cancers are diagnosed at a stage when the option of a curative surgical resection is not available. Presently, no current imaging studies including high-resolution CT, MRI, endoscopic ultrasound (EUS), and endoscopic cholangiopancreatography (ERCP) can reliably detect pancreatic tumors at potentially resectable stage. Current imaging modalities as well as ERCP utilize the presence of a mass lesion, and, therefore, even if the resolution of these tests is improved, the tumor detected is likely biologically too advanced for cure.

Despite years of research, no clinically effective molecular markers have been developed. Importantly, widespread pancreatic cancer screening by means of examination of the pancreatic duct (e.g., ERCP) is not feasible given that interrogation of the pancreatic duct including biopsy, fiber-optic evaluation, and/or brushing may lead to serious complications in ~20% cases, including acute pancreatitis (~5%), which is a potentially life-threatening condition. Thus, this approach may not be suitable for routine screening over successive points in time but may be appropriate for selective situations in which the suspicion for an advanced precursor lesion or early staged tumor is high.

SUMMARY OF THE DESCRIPTION

Systems, methods, and apparatuses of elastic light scattering spectroscopy and low-coherence enhanced backscattering spectroscopy are described here. Some embodiments of the present disclosure are summarized in this section.

In one aspect, embodiments of the present disclosure includes an apparatus couple-able to a light source and a target object, to facilitate light transmission between the light source and the target object, the apparatus comprising a probe to emit incident light that is partially coherent obtained from the light source onto the target object and to receive interacted light, the interacted light to be backscattered light from illumination of the incident light on the target object, the probe comprising: a delivery channel having at least one delivery optical fiber with a distal end portion couple-able to the light source and a proximal end portion suited to couple the incident light to the target object, a collection channel having a first collection optical fiber suited to collect substantially co-polarized backscattered light and a second collection optical fiber suited to collect substantially cross-polarized backscattered light, the first collection optical fiber and the second optical fiber each having a proximal end portion to receive the light to be backscattered from illumination of the partially coherent light on the target object, and a distal end portion adapted to be coupled to a receiving end, and a plurality of optical components optically coupled to the proximal end portion of one or more of the at least one delivery optical fiber, the first collection optical fiber and the second collection optical fiber.

In another aspect, embodiments of the present disclosure include a method for measuring the properties of a target object comprising, recording an intensity of at least one spectral component and at least one angular component of backscattering angle of backscattered light, wherein the backscattered light is to be backscattered from illumination of incident light on a target object, selecting a depth of penetration of the target object by the incident light via adjusting a spatial coherence length of the incident light, wherein the depth of penetration is to be determined based on characteristics of the target object, and further recording an intensity of at least one azimuth angle of the at least one spectral component and the at least one angular component of the backscattering angle of the backscattered light, wherein the backscattering angle is an angle between backscattered light propagation direction and incident light propagation direction, and the azimuth angle is an angle between incident light polarization and projection of the direction of the incident light onto a plane in which electric field of the incident light oscillate.

In yet another aspect, embodiments of the present disclosure include a means for, recording an intensity of one or more of at least one spectral component and at least one angular component of backscattering angle of backscattered light, wherein the backscattered light is to be backscattered from illumination of incident light on a target object, a means for, selecting a depth of penetration of the target object by the incident light via adjusting a spatial coherence length of the incident light, wherein the depth of penetration is to be determined based on characteristics of the target object, and a means for, further recording an intensity of at least one azimuth angle of the one or more of at least one spectral component and the at least one angular component of the backscattering angle of the backscattered light, wherein the backscattering angle is an angle between backscattered light propagation direction and incident light propagation direction, and the azimuth angle is an angle between incident light polarization and projection of the direction of the incident light onto a plane in which electric field of the incident light oscillates.

In one aspect, a method for measuring the properties of a target object includes recording an intensity of at least one spectral component and/or at least one angular component of backscattered light. The backscattered light can be backscattered from illumination of incident light on a target object in vivo. In one embodiment, an intensity of at least one azimuth angle of at least one spectral component and/or the at least one angular component of the backscattered light is recorded. The backscattering angle is an angle between backscattered light propagation direction and incident light propagation direction, and the azimuth angle is an angle between incident light polarization and projection of the direction of the incident light onto a plane in which electric field of the incident light oscillates.

In one embodiment, an intensity of at least one polarization of the at least one spectral component and/or the at least one angular component of the backscattering angle of the backscattered light is recorded. The at least one polarization is co-polarized or cross-polarized to the incident light polarization. The co-polarized backscattered light is approximately parallel to the incident light polarization and cross-polarized backscattered light is approximately perpendicular to the incident light polarization.

In one embodiment, the intensity of the at least one spectral component and/or the at least one angular component of the backscattering angle of backscattered light is analyzed to obtain a first set of optical markers of the backscattered light, toward evaluating said properties. In one embodiment, the backscattered light is low coherence enhanced backscattered light. The first set of optical markers includes spectral markers and/or angular markers. The angular marker may be a decay rate of a Fourier transform of the intensity of the at least one angular component of the backscattered light with respect to an independent Fourier variable of the Fourier transform. In one embodiment, the angular marker is a correlation decay rate of the intensity of the at least one angular component of the backscattered light.

In one embodiment, the angular marker is a correlation decay rate of the intensity of the at least one angular component of the backscattered light. In one embodiment, the angular marker is an angular width and/or an enhancement factor of the intensity of the at least one angular component of the backscattered light. In one embodiment, the spectral marker is a spectral slope, a correlation decay rate, and/or the principal components of the intensity of the at least one spectral component of the backscattered light. The spectral marker may be a spectral exponential of the at least one spectral component of the backscattered light.

In one embodiment, the intensity of the at least one azimuth angle of the at least one spectral component and/or the at least one angular component of the backscattering angle of backscattered light is analyzed to obtain a second set of optical markers of the backscattered light, toward evaluating said properties. In one embodiment, the second set of optical markers of the backscattered light is obtained via analyzing the intensity of the at least one polarization of the at least one spectral component and the at least one angular component of the backscattering angle of the backscattered light.

In one embodiment, the second set of optical markers includes spectral markers and/or angular markers. The angular marker may be a decay rate of a Fourier transform of the intensity of the at least one angular component of the backscattered light with respect to an independent Fourier variable of the Fourier transform. In one embodiment, the angular marker is a correlation decay rate of the intensity of the at least one angular component of the backscattered light. The angular marker may be at least one of an angular width and enhancement factor of the intensity of the at least one angular component of the backscattered light.

In one embodiment, the spectral marker is a spectral slope, a correlation decay rate, a fractal dimension, and/or at least one principal component of the intensity of the at least one spectral component of the backscattered light. The spectral marker is a spectral exponential of the at least one spectral component of the backscattered light.

In one embodiment, the incident light to be illuminated on the target object in vivo is provided. The incident light may include at least one spectral component having low coherence. In one embodiment, a spatial coherence length of the incident light is adjusted to select a depth of penetration of the target by the incident light. The incident light can be projected onto the target having an angle of incidence greater than zero degrees to mitigate specular reflection from the target. The angle of incidence is the angle between the incident light propagation direction and a direction normal to the target.

In one embodiment, at least one spectral component of the backscattered light is collected to detect backscattered light having low temporal coherence length. The recording may include simultaneous measurement of the at least one spectral component and the at least one angular component of the backscattering angle of the backscattered light and recording a matrix of intensities of backscattered light as a function of wavelength and backscattering angle. The depth of penetration is approximately the spatial coherence length of the incident light.

In one embodiment, the depth of penetration of the incident light is determined based on at least one angular component of the backscattering angle of the backscattered light. A large angular component of the backscattering light may correspond to a small depth of penetration of the incident light and a small angular component of the backscattering light may correspond to a large depth of penetration of the incident light. Further, the depth of penetration of the target by the incident light based on a probability of radial distribution intensity of the backscattered light.

In one embodiment, the target object is at least a portion of the living subject. The sample may be a biological sample. The biological sample may include tissue undergoing neoplastic transformation. Further, the neoplastic transformation may be cancer. The cancer can be pancreatic cancer, colon cancer, liver cancer, lung cancer, esophageal cancer, stomach cancer, cervical cancer, oral cavity cancer, ovarian cancer, breast cancer, bladder cancer, cholangiocarcinoma, prostate cancer, and/or head and neck cancer In one embodiment, an image of the target object is acquired. The depth of penetration of the target object by the incident light where the optical marker of the backscattered light is sensitive to biological changes of the target object can be identified.

In one embodiment, the optical marker from non-neoplastic tissue can be obtained to detect one or more of adenoma and carcinoma of tissue obtained from a different anatomic portion than the non-neoplastic tissue. The optical marker from tissue of an anatomical region at least one of a proximal and distal to tissue of the anatomical region potentially harboring one or more of adenoma and carcinoma can be obtained.

In one embodiment, presence of one or more of adenoma and carcinoma in at least a part of the colon is detected via detecting optical changes via at least one optical marker from tissue obtained from anywhere in the colon. For example, the tissue can be obtained from the anywhere in the colon including a cecum, ascending colon, hepatic flexure, transverse colon, splenic flexure, descending colon, sigmoid colon, and/or rectum. In one embodiment, the tissue is endoscopically normal or histologically normal.

In one embodiment, pancreatic neoplasia is detected via detecting optical changes via at least one of the first set and the second set of optical markers obtained from non-neoplastic tissue. The non-neoplastic tissue may be the duodenal periampullary mucosa. The non-neoplastic tissue can be tissue affected by at least one of a genetic and environmental milieu to result in the pancreatic neoplasia. In addition, the non-neoplastic tissue is endoscopically normal and/or histologically normal.

The present disclosure includes methods and apparatuses which perform these methods, including processing systems which perform these methods, and computer readable media which when executed on processing systems cause the systems to perform these methods.

In an alternative embodiment, the methods of the present invention may be employed in a bench-bound environment, such as when a closer examination of a patient's tissue may be warranted. In such a situation, the light emitting element may be a stationary or more or less stationary apparatus, as opposed to a hand-held probe.

Other features of the present disclosure will be apparent from the accompanying drawings and from the detailed description which follows.

BRIEF DESCRIPTION OF THE DRAWINGS

The disclosure is illustrated by way of example and not limitation in the figures of the accompanying drawings in which like references indicate similar elements.

FIG. 7A is an intensity plot of LEBS signals recorded from histologically and/or endoscopically normal tissue in the AOM-treated rat model and a control rat, according to one embodiment, according to one embodiment.

FIG. 7B-C are intensity plots of ELF signals recorded from histologically and/or endoscopically normal tissue in the AOM-treated rat model and a control rat, according to one embodiment, according to one embodiment.

FIG. 10 is a table showing performance characteristics of ELF and LEBS optical markers obtained from histologically and/or endoscopically normal duodenal periampullar mucosa for detection of pancreatic cancer, according to one embodiment.

FIG. 12 is a table showing performance characteristics of ELF and LEBS optical markers obtained from histologically and/or endoscopically normal rectal mucosa of rats, according to one embodiment.

FIG. 17 is a table showing results of correlation analysis between a patient's age and ELF and LEBS markers, according to one embodiment.

DETAILED DESCRIPTION

Figure 1:
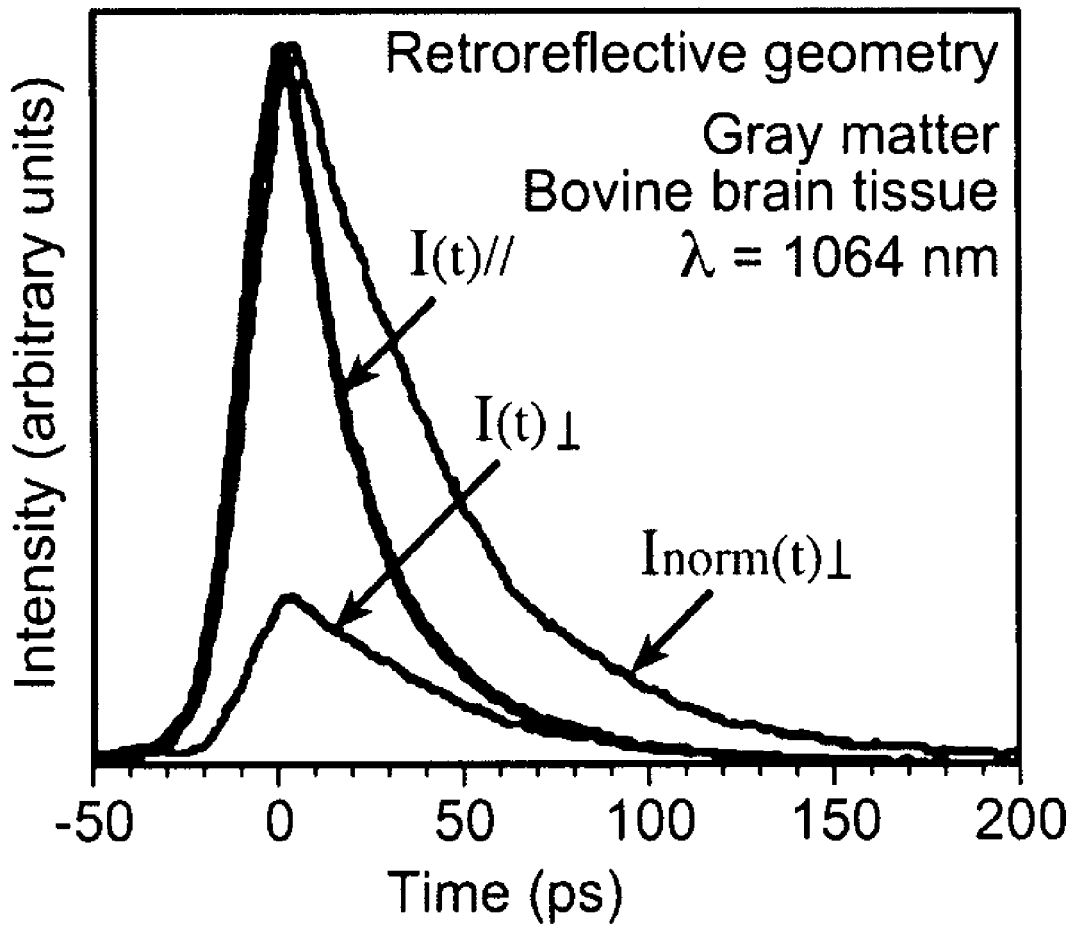
FIG. 1A illustrates a plot of the temporal profiles of two polarization components of backscattered light, according to one embodiment.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Without intent to limit the scope of the disclosure, exemplary instruments, apparatus, methods and their related results according to the embodiments of the present disclosure are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the disclosure so long as the disclosure is practiced according to the disclosure without regard for any particular theory or scheme of action Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Embodiments of the present disclosure include systems, methods, and apparatuses of elastic light scattering spectroscopy and low-coherence enhanced backscattering spectroscopy.

In one aspect, the present disclosure relates to optically examining a target object for early detection of pre-neoplastic changes based on the field effect, or the concept that genetic/environmental milieu that results in a neoplastic lesion in one area of an anatomical region should be detectable in uninvolved (e.g., normal-appearing) mucosa throughout the anatomical region. For example, presence of pancreatic neoplasia can be diagnosed via examination of the duodenal periampullary mucosa adjacent to the opening of the pancreatic duct (e.g., ampulla) which is readily accessible by existing upper endoscopy techniques, thereby preventing potential complications such as pancreatitis caused by more invasive imaging means. Due to the field effect, the endoscopically and/or histologically normal duodenal tissue can reflect presence of pancreatic neoplasia in the optical data obtained.

In one aspect, optical data obtained from elastic light scattering spectroscopy (e.g., four-dimensional light scattering spectroscopy, or 4D-ELF) and low-coherence backscattering (LEBS) spectroscopy are combined, to in situ detect subtle histologically and/or endoscopically undetectable changes in tissue nano/micro-architecture associated with carcinogenesis. The combination and analysis of the two sets of optical data can improve the sensitivity to detect tissue changes associated with carcinogenesis over either optical spectroscopy techniques when used separately.

In one aspect, the two optical techniques can be employed in a common probe. For example, a probe comprises a light source configured and positioned to project light on a target object, a means to measure at least one spectral component of light scattered from the target object, and at least one angular component of light scattered from the target object. The probe apparatus may further include a detector to obtain the spectral data of the backscattered light. The spectral data can then be analyzed to determine if the target object having the tissue to be inspected is normal.

In one aspect, the two optical techniques can be employed to examine tissue ex vivo either with common instrumentation or separate instruments. The diagnosis can be based on data obtained separately from elastic light scattering spectroscopy and from low-coherence backscattering spectroscopy. For example, the duodenal periampullary mucosa obtained during upper endoscopy can be examined ex vivo by the two optical techniques.

Neoplastic disease is at least part of a process leading to a tumor or lesion, where the tumor or lesion can be an abnormal living tissue (e.g., premalignant or cancerous), such as pancreatic cancer, a colon cancer, an adenomatous polyp of the colon, a liver cancer, a lung cancer, a breast cancer, and/or other cancers. While abnormal tissue can be a lesion or tumor, the abnormal tissue can also be tissue that precede the development of dysplastic lesions that themselves do not yet exhibit dysplastic phenotype, and tissues in the vicinity of these lesions or pre-dysplastic tissues.

A particular application described herein is for detection of such pre-neoplastic changes in the pancreas and the colon in early pancreatic cancer and colon cancer detection, other applications are described as well. Other biologically related application include monitoring of bioengineered tissue development. Yet other applications are contemplated beyond use of the invention in association with healthcare, such as characterization of polymer mechanical and molecular weight data, morphological structures of solid polymeric materials Field Effect Some cancer risk stratification techniques exploit the "field effect," the concept that assessment of biomarkers in one area of the colon should be able to determine the likelihood of current/future neoplastic lesions throughout the colon. For example, the genetic/environmental milieu that results in a neoplastic lesion in one area of the colon can be detectable in uninvolved (i.e., colonoscopically, histologically, and/or endoscopically normal-appearing) mucosa throughout the colon.

There exists evidence to support the molecular underpinnings of the microarchitectural changes noted in the histologically and/or endoscopically normal "field." For instance, Chen et al. recently reported that a panel of proto-oncogenes, including cyclooxygenase 2 and osteopontin, were markedly over expressed in histologically and/or endoscopically normal mucosa of patients harboring colorectal cancer. This is also noted in the preneoplastic MIN mouse and, importantly, the magnitude of proto-oncogenes over-expression was in-between control intestinal epithelium (C57BL/6 mice wild type at APC) and adenomatous tissue or carcinomous tissue, arguing for the relevance of these changes to tumorigenesis. Furthermore, work by Cui et al. have noted that another epigenetic event (e.g., loss of insulin growth factor II imprinting) was increased in the uninvolved mucosa of patients with who harbored adenoma or carcinomas.

A commonly used clinical example is the identification of the distal adenoma or carcinoma on flexible sigmoidoscopy to predict the occurrence of neoplasia in the proximal colon. Other attempts include correlation of rectal aberrant crypt foci (ACF) using chromoendoscopy with colonic adenomas and carcinomas. Unfortunately, the performance characteristics of the existing markers remain suboptimal (e.g., the sensitivity and positive predictive value for the ability of flexible sigmoidoscopy to detect advanced proximal lesions are 40% and 6%, respectively.

Thus, currently available morphologic markers for the field effect are inadequate for risk stratification. Several lines of evidence suggest that the field effect has the potential of being sensitive at identifying patients with colonic neoplasia. Studies have reported that in the histologically and/or endoscopically normal mucosa of subjects harboring colonic neoplasia, there are profound genetic and epigenetic alterations in the field effect. However, detecting these molecular events with a methodology that would be feasible in clinical practice has been challenging.

It has been demonstrated by LEBS technology to identify colon carcinogenesis risk throughout the colon through detection of the field effect. Data obtained from azoxymethane-treated rat model of colon carcinogenesis show alterations in LEBS markers at time points that precede ACF or adenoma or carcinoma formation. Furthermore, these markers progress over time consonant with the progression of carcinogenesis. These results were replicated in the genetic model of intestinal carcinogenesis (the MIN mouse).

In human studies, LEBS analysis of the endoscopically normal mucosa is observed to be able to detect differences in patients who harbored adenoma or carcinomas when compared with those who were neoplasia free. Thus, the technical advance of LEBS may potentially translate into a practical means for colon cancer screening. As discussed, the exploitation of the field effect is a strategy in colorectal cancer screening (e.g., assessment of distal adenoma or carcinomas or ACF). To improve sensitivity, others have proposed looking at cellular (apoptosis and proliferation) and biochemical variables (e.g., protein kinase C); however, the performance characteristics still lack suitability for clinical practice.

In one embodiment, the analysis of mucosal nanoarchitectural and microarchitectural markers by means of LEBS exceeded the classic morphologic and/or biochemical markers. For example, the risk of neoplasia was assessed in the visually normal colonic mucosa rather than to detect morphologic lesions polyps. The neoplastic transformation may lead to various types of cancer, such as pancreatic cancer, colon cancer, liver cancer, lung cancer, esophageal cancer, stomach cancer, cervical cancer, oral cavity cancer, ovarian cancer, breast cancer, bladder cancer, cholangiocarcinoma, prostate cancer, and/or head and neck cancer, which can be detected via LEBS screening.

Four-Dimensional Elastic Light Scattering Fingerprinting (4D-ELF)

Light scattering spectroscopy (LSS) is based on the principle that the intensity of light elastically scattered (i.e., without change in wavelength) from a tissue is a function of the composition of both light absorbers and scatterers within the tissue. Light absorption is often governed by molecules such as hemoglobin, whereas scattering can be determined by the sizes and densities of space-occupying structures including cell organelles and macromolecular complexes. An extension of LSS, 4D-ELF allows acquisition of light-scattering data in several dimensions, thus providing unprecedented insights into tissue composition.

The dimensions of 4D-ELF include (1) wavelength of light, (2) the scattering angle (i.e., the angle between the backward direction and the direction of the propagation of scattered light), (3) azimuthal angle of scattering (i.e., the angle between the incident light polarization and the projection of the direction of the scattered light propagation onto the plane in which the incident electric field oscillates), and (4) polarization of scattered light.

In polarization gating, polarized light illuminates a particular site on the surface of a sample, such as biological tissue, and the returned elastic scattering signal can be split into two components with polarizations parallel (e.g., co-polarized signal) or orthogonal (cross-polarized signal) to that of the incident light, respectively. The co-polarized signal is generated by both low order scattering (e.g., primarily from scatterers located close to the surface) and multiple scattering (e.g., primarily from scatterers located deeper into the medium). On the other hand, the cross-polarized signal is predominantly generated by the multi-scattered photons from the deeper layers of the medium.

FIG. 1 illustrates a plot of the temporal profiles of two polarization components of backscattered light, according to one embodiment.

The temporal profiles of the backscattered light were recorded with a linearly polarized light source at 1064 nm. and pulsed at 6.5 ps. The light source was used to illuminate bovine gray matter brain tissue. As shown, the two profiles have different peak values, temporal location of the peak value, and the width of the intensity curve (e.g., the full-width at half maximum). The peak intensity value of the parallel polarization component is higher than the peak of the perpendicular polarization. The peak of the perpendicular component also appears later in time than the parallel component. The width of the parallel component is smaller that of the perpendicular component.

The discrepancies between the parallel and perpendicular components are due to the multi-scattering events of the backscattered photons that are perpendicularly polarized, due to the fact that sufficient backscattering should occur before polarization is lost, as in the case of perpendicular polarization.

Since the photons backscattered from the surface of the tissue scatterers and hence less depolarization, the backscattered photons from the surface and initial layers beneath the surface tend to be polarized parallel (e.g., co-polarized) to the incident light. Since the perpendicular polarization component includes photons that have penetrated the sample, the perpendicular intensity peak may be less intense. The peak intensity of the perpendicular component also tends to have a delay in time due to photons penetrating in the sample and back.

Because multiple scattering depolarizes scattered light, the sensitivity to the low-order scattering component can be increased by subtracting off the depolarized multiple scattering signal. This can be achieved by subtracting $I_{perpendicular}$ from $I_{parallel}$. The resulting signal $\Delta I = I_{parallel} - I_{perpendicular}$ is referred to as the differential polarization signal and is predominately determined by the single and/or low order scattering in the superficial layer of the scattering medium.

The polarization-sensitive detection allows penetration depth selectivity. Most biological tissues are relatively turbid. Light propagation in such media is dominated by the multiple scattering from tissue structures located within several millimeters of the tissue surface, as in the case of colon tissue including both the mucosa and submucosa. The single scattering collected by means of polarization gating is primarily contributed by scatterers located close to the tissue surface and therefore sensitive to the properties of the superficial tissues (e.g., the epithelia).

The differential polarization signal ($\Delta I = I_{parallel} - I_{perpendicular}$) is primarily contributed by the superficial tissue structures located within approximately 30-50 µm of the tissue surface, which typically includes the epithelial cell layer. The co-polarized signal $I_{parallel}$, diffuse reflectance signal $I_{parallel} + I_{perpendicular}$, and the cross-polarized signal $I_{perpendicular}$ provide information about progressively deeper tissues (up to several millimeters below the surface). Light scattering and absorption by red blood cells may alter the differential polarization signals $\Delta I$, which characterize tissue nanoarchitecture and microarchitecture.

Because differential polarized signals are superpositions of single scattering contributions from various tissue scatterers within the superficial tissue, the signals from red blood cells in rat tissue samples can be subtracted from the unprocessed light-scattering spectra by fitting the red blood cell signals to $\Delta I$. Although unpolarized diffuse reflectance tissues have previously been studied, the information obtained regarding tissue structures is averaged over several photon transport paths (approximately several millimeters), which does not allow characterization of epithelial and near-epithelial tissues. On the other hand, polarization gated measurements, can provide principally information about changes in organization of epithelial cells, which is crucial for detection of the initial stages of carcinogenesis.

Elastic Light-Scattering Optical Markers

Elastic light-scattering optical markers are able to convey information about tissue microarchitecture and nanoarchitecture. A number of light-scattering signatures can be linked to properties of cell architecture, including the size distribution of intraepithelial nanoscale and microscale structures (e.g., from ~30-40 to 800 nm) and the fractal dimension of the cell structure at supramicro scales (e.g., greater than ~1 µm). The combination of these measures enables quantitative characterization of epithelial architecture in a wide range of scales, from tens of nanometers to microns.

For example, to obtain the complete size distribution of subcellular structures at each tissue site, the spectra that is computationally simulated using Mie theory can be fit to the differential polarization tissue spectra for a given scattering angle and azimuth of scattering using conventional least-squares minimization algorithm.

Spectral Slope

The change in backscattered light intensity, or $\Delta I(\lambda)$ with wavelength of the light depends on the size distribution of scattering structures. Generally, $\Delta I(\lambda)$ is a declining function of wavelength and its steepness is related to the relative portion of structures of different sizes. Larger structures can to reduce the steepness of the decline of $\Delta l(\lambda)$, whereas smaller scatterers tend to make $\Delta l(\lambda)$ decrease with steeper wavelength. To analyze the data and characterize the spectral variations of $\Delta l(\lambda)$, linear fits to $\Delta l(\lambda)$ using linear regression analysis can be obtained. The absolute value of the linear coefficient of the fit, referred to as the spectral slope, quantifies the dependence of the scattering spectrum on wavelength and can serve as a marker to characterize the distribution of structures within the cells.

For example, the spectral slope can be obtained as the absolute value of the linear coefficient of the linear fit to $\Delta l(\lambda,\theta,\phi)$ for fixed $\theta$ and $\phi$ (e.g., $\Delta l(\lambda,\theta,\phi)$ can be integrated over $\theta$ for $\phi=0$, $\lambda=500-650$ nm). The spectral slope depends on the size distribution of scattering structures: abundance of smaller (up to 40 nm) scatterers increases the spectral slope.

Spectral Exponential

Similarly l(k) can vary based on the exponential power of the wavelength. For example $I(k) \propto \lambda^{-\alpha}$, where $\alpha$ is referred to as the spectral exponential.

Fractal Dimension

The angular distributions of the 4D-ELF signatures can be used to calculate the fractal dimension of tissue microarchitecture, which characterizes cell structures at scales greater than 1 micrometer. To estimate the fractal dimension, the angular distribution at 550 nm. was first Fourier transformed to generate the two-point mass density correlation $C(r)=<\rho(r)\rho(r+r')>$ where $\rho(r)$ is the local mass density at the spatial point r, which is proportional to the concentration of intracellular solids, such as DNA, RNA, and proteins. C(r) can be approximated as the power-law ($C(r)=r^{D-3}$) for r ranging from 1 micrometer to 50 micrometers, where D is referred to as fractal dimension. D was obtained from the linear slope of C(r) in the log-log scale.

Fourier Transform of $I(\theta)$

The Fourier transform of the angular profile $I(\theta)$ can be used to calculate the decay rate of the transform with respect to the independent Fourier variable. For example, the decay rate is $$\frac{d}{dr}P(r),$$

where $P(r)=FT\{I(\theta)\}$.

The decay rate can be sensitive to optical properties of tissue architecture, such as scattering coefficient and optical density.

Principle Component Analysis

Data generated by elastic light scattering can be further analyzed through principal component analysis (PCA). PCA has been used for biological and clinical purposes, such as assessment of karyotypic alterations and distinct biological features (e.g., global molecular phenotype) in human colon cancer. This variable reduction procedure can be useful in assessing underlying structure in a complex data set. Because principal components are extracted in a stepwise fashion, the first principal component is responsible for the largest variance.

It has now been discovered that principal component 1 (PC1) can be a marker of the field effect that may be exploited for colorectal cancer screening. For example, the light-scattering spectra can be averaged over a predetermined range of backscattering angle (e.g., scattering angles from −5° to 5°) and the spectral components can be preprocessed by mean scaling.

Coherent Backscattering (CBS)/Enhanced Backscattering (EBS)

Coherent backscattering (e.g., enhanced backscattering, CBS, or EBS) of light, originates from the constructive interference in elastic light scattering that gives rise to an enhanced scattered intensity in the backward direction. For a plane wave illuminating a semi-infinite random medium, photons scattered from the medium in the backward direction has a time-reversed photon traveling along the same path in the opposite direction (e.g., the path formed by exactly opposite sequences of the scattering centers). These photons have the same phase and thus interfere constructively with each other, resulting in an enhanced backscattering peak.

Constructive interference occurs in the backscattering direction, whereas in directions sufficiently away from the backward direction, the constructive interference vanishes. In some situations, the peak EBS intensity can be twice as high as the incoherent intensity scattered outside the EBS peak (or background intensity).

The enhanced backscattering phenomenon can be investigated in a variety of different systems such as strong scattering materials, laser-cooled atoms, liquid crystals, photonic crystals, amplifying materials, and/or solar system bodies. Although the EBS phenomenon has attracted significant attention and can be observed in variety of nonbiological media, there has been few reports on EBS in biological tissue.

The lack of applications to biological samples may be due to the characteristics of EBS including: 1) conventional EBS peaks in tissue are narrow with angular width $w \approx \lambda/(3\pi l_s^*)$ ~0.001°, where $\lambda$ is the wavelength of light and $l_s^*$ is transport mean free path (in tissue $l_s^* \sim 500\text{-}2000$ μm). Experimental observation of such narrow peaks can be difficult. 2) EBS can be masked by speckle. 3) EBS measurements have not been shown to provide spectroscopic information, which is crucial for tissue diagnosis. 4) Conventional EBS does not enable depth-resolution. However, since most tissues have multi-layered structures, depth-resolution can be crucial for tissue diagnosis.

The enhanced backscattering peak profile can be further characterized by the distribution of path lengths of backscattered photons. For example, the dependency of the profile of the enhanced backscattering peak on the distribution of the path length can be studied using femtosecond-resolved measurements. Because the angular width of an EBS peak is proportional to the ratio of wavelength of light to the transport mean free path of light in the medium in biological tissue, the width of the EBS peak in tissue is narrow, typically w~0.001 degrees (w is the angular full width at half maximum of an EBS peak).

Quantitatively, the angular profile of an EBS peak $I_{EBS}(\theta)$ can be expressed as a 2-D Fourier transform of the radial intensity distribution of EBS:

$$I_{EBS}(\theta) \propto \int_0^\infty rP(r)\exp(i2\pi\theta/\lambda)\,dr$$

Thus, $I_{EBS}(\theta)$ is the Fourier transform of radial intensity probability distribution rP(r) of the backscattered photons. As a result, in an EBS peak, longer light paths correspond to small scattering angles, while shorter light paths correspond to larger scattering angles.

Low-Coherence Enhanced Backscattering (LEBS)

In principle, in EBS, the conjugated time-reversed waves can interfere with each other when they are spatially coherent, that is, the first and last points on the scattering path are within the coherence area. Some EBS measurements have been conducted using coherent laser light sources with spatial coherence length $L_{SC} \gg l_s^*$. Under such spatially coherent illumination, conjugate time-reversed waves emerging from the surface of the sample can be capable of interfering with each other.

However, if light incident on a sample has a finite spatial coherence length, the conjugated time-reversed waves can interfere constructively with each other when they are spatially coherent. Thus, the angular profile of an EBS intensity $I_{EBS}(\theta)$ can be expressed as:

$$I_{EBS}(\theta) \propto \int_0^\infty C(r) r P(r) \exp(i 2\pi \theta / \lambda) \, dr$$

A finite spatial coherence area acts as a spatial window rejecting long paths by preventing long traveling waves from interfering with each other. In other words, spatial coherence length limits r contributing to the EBS signal. Incoherent waves have no correlation in phase and generate the incoherent background intensity. Thus, if $L_{SC}$ is sufficiently short (e.g., $L_{SC} \ll l_s^*$) the low spatial coherence illumination can enable low-order scattering to contribute to the EBS peak, resulting in significant (e.g., several orders of magnitude) broadening of an EBS peak.

Characteristics of Low-Coherence Enhanced Backscattering Spectroscopy (LEBS)

Spectroscopic Measurements

Using LEBS spectroscopy, intensity profiles can be observed as a function of wavelength. Simultaneous measurement of the spectral and scattering angle distributions of backscattered light can enable simultaneous recording of the spectral (e.g., 400-700 nm) and scattering-angle (e.g., −7° to 7° from the backscattering direction) distributions of scattered light.

Figure 2A:
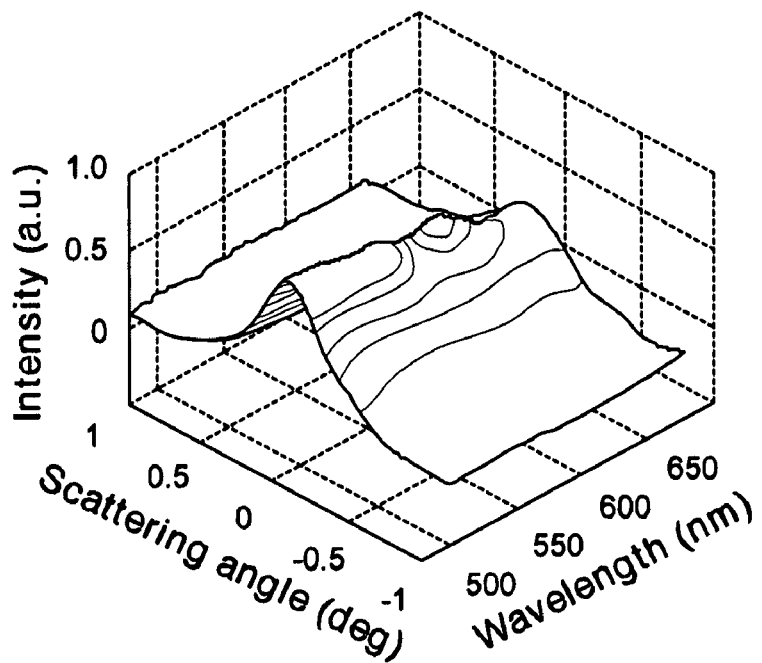
FIG. 2A illustrates a plot of low coherence enhanced (LEBS) backscattering intensity recorded from a rat colon tissue as a function of wavelength and scattering angle, according to one embodiment.

FIG. 2A illustrates a plot of LEBS backscattering intensity recorded from a rat colon tissue as a function of wavelength and scattering angle, according to one embodiment.

Several optical spectroscopic techniques have been demonstrated to be useful for tissue diagnosis and characterization including reflectance, light scattering, fluorescence, and other types of spectroscopy. Consequently, the analysis of LEBS spectra may be used to provide additional information about tissue architecture, its tissue characterization and diagnosis.

Speckle Reduction

Figure 2B:
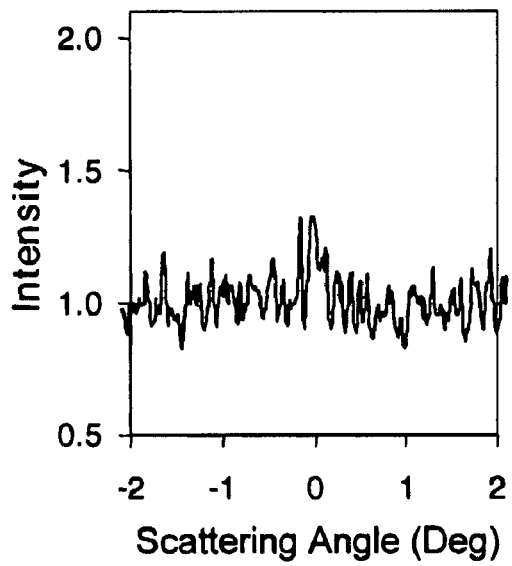
FIG. 2B illustrates a plot of the backscattering intensity as a function of the scattering angle in conventional enhanced backscattering (EBS), according to one embodiment.

Experimental observation of LEBS may include ensemble or configuration averaging because of speckle, which arises from random interference effects. For example, rotating the sample mechanically or averaging independent measurements are used in conventional EBS measurements. Speckle becomes more severe in the absence of Brownian motion, hampering EBS studies in biological tissue. However, LEBS overcomes this problem. For comparison, FIG. 2B illustrates a plot of the backscattering intensity as a function of the scattering angle in conventional EBS, according to one embodiment.

The angular distribution of the backscattered light obtained from the same tissue site when a coherent He—Ne laser was used is shown. As can be seen, in the case of coherent illumination, the speckle masks the profile of an EBS peak. It has been shown that both low spatial and temporal coherence can contribute to speckle reduction. For example, for $L_{SC} \sim 150$ µm, the number of independent coherence volumes $(D/L_{SC})^2 \times (l/L_{SC}) \sim 1000$, where D is the diameter of illumination area on the sample and l is the average path length. Therefore, LEBS measurements can be easily achieved in random media, even in the absence of Brownian motion without the need for ensemble or configuration averaging.

Figure 2C:
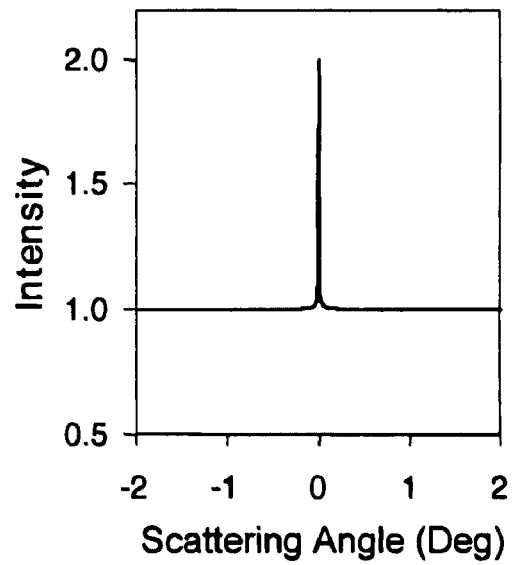
FIG. 2C illustrates a plot of the backscattering intensity as a function of the scattering angle in LEBS which is speckle-free, according to one embodiment.

FIG. 2C illustrates a plot of the backscattering intensity as a function of the scattering angle in LEBS which is speckle-free, according to one embodiment.

As can be seen, in the case of the LEBS signal recorded from the same tissue site, speckle is negligible and an enhanced backscattering peak can be identified. Both low spatial coherence illumination and low temporal coherence detection contribute to speckle reduction.

Broadening of Enhanced Backscattering Peaks

Broadening of EBS under low coherence illumination facilitates experimental observation of LEBS. Since the width of a conventional EBS peak in general is inversely proportional to ls*, the width of an EBS peak in tissue and other random media with long ls* is narrow, typically w~0.001 deg. On the other hand, an LEBS peak is broader with w~0.5 deg, which is approximately more than 100 times greater than the width of a conventional EBS peak expected under spatially coherent illumination. The width of LEBS is increased because it is predominantly generated by photons traveling short paths, restricted by a short spatial coherence length.

Depth-Selective Low-Coherence Enhanced Backscattering Measurements

Low spatial coherence illumination rejects long traveling paths and enables low-order scattering to contribute to the EBS thus allowing selectively probing superficial tissue. Because the superficial tissue layer (i.e., the epithelium) which can be as thin as 20-40 µm, is typically the first affected in carcinogenesis. For example, selective probing of CRC-significant cells, such as the colon stem cells in the base of the crypt can be achieved via LEBS examination.

In addition, hemoglobin (Hb) absorption in the blood vessels located underneath epithelium, but not within epithelium can obscure the endogenous spectral signatures of epithelial cells. This difficulty can be resolved using depth selectivity of LEBS.

Depth-selective LEBS spectroscopy of tissue can be achieved by three means: 1. Varying coherence length $L_{SC}$, 2. Analysis of LEBS spectra $I_{EBS}(\theta)$ at different scattering angles, and 3. Analysis of the radial intensity probability distribution of LEBS photons P(r), which can be obtained via the Fourier transform of $I_{EBS}(\theta)$. In brief, $L_{SC}$ determines the maximum penetration depth. Then, detailed depth-resolution can be obtained by either means 2 or 3.

Control of Tissue Depth Probed with LEBS Via Coherence Length

Photons emerging from the tissue surface at distances $r < \sim L_{SC}$ from the point of entry into the tissue can more effectively contribute to LEBS. Thus, the depth of penetration of LEBS photons is approximately $\sim L_{SC}$.

Control of Tissue Depth Probed with LEBS Via the Analysis of $I_{EBS}(\theta)$ at Different θ

Because $I_{EBS}(\theta)$ is the Fourier transform of P(r), short light paths (e.g., small r) mainly give rise to the periphery of an LEBS peak (e.g., large θ), while longer light paths (r~$L_{SC}$) give rise to the top (or center) of the LEBS peak (θ→0 deg). This property of LEBS can be used to sample various depths using a single LEBS measurement by analyzing $I_{EBS}(\theta)$ at different θ.

Small θ corresponds to deeper penetration depths, whereas large θ corresponds to shorter depths. Therefore, different depths can be selectively assessed by probing a corresponding scattering angle. For example, in the case of colonic mucosa, $I_{EBS}(\theta=0.25 \text{ deg})$ enables assessment of an epithelial cell layer (~40 μm), whereas $I_{EBS}(\theta=0 \text{ deg})$ allows probing the entire mucosa (~70 μm).

Control of Tissue Depth Probed with LEBS Via the Analysis of P(r) at Different r Tissue depths from ~40 μm (e.g., a single cell layer) to ~100 μm (e.g., thickness of colonic mucosa) can be selectively assessed by means of the analysis of $P(r, \lambda)$ by choosing appropriate parameter r. Thus, LEBS spectroscopy enables the possibility of performing spectroscopic measurements at any given depth within the maximum penetration depth determined by $L_{SC}$.

A more precise control of tissue depth probed with LEBS can be achieved by means of the analysis of P(r), which can be obtained from the Fourier transform of $I_{EBS}(\theta)$. Thus, the depth of penetration of photons increases with r.

To investigate depth selectivity with LEBS, a two layer tissue phantom was prepared as solid phantom and comprises agarose gel-imbedded suspension of red blood cells to mimic light absorption in tissue and 0.43 μm polystyrene microspheres to mimic tissue scattering.

The significance of depth-selective spectroscopic measurements for tissue characterization and diagnosis is underscored by the following reasons.

1. The most superficial tissue layer (i.e., the epithelium) is the origin of nearly 90% of human cancers and the epithelial cells are the first affected in carcinogenesis. Thus, obtaining diagnostic information from most superficial tissue is crucial for the early diagnosis of epithelial precancerous lesions.

2. Hemoglobin absorption in the blood vessels located underneath the epithelium is a particularly notorious problem, as it obscures the endogenous spectral signatures of epithelial cells.

3. The depth-dependent biological heterogeneity of the epithelium underscores the need to selectively assess the epithelial cells at different depths. For example, in the colon (the major unit of organization of the mucosa is the crypt), the epithelial cells at the base of the crypt (~80 μm below the tissue surface) are capable of proliferation, while the epithelial cells at the top of the crypt (~40 μm) undergo apoptosis.

Figure 3A:
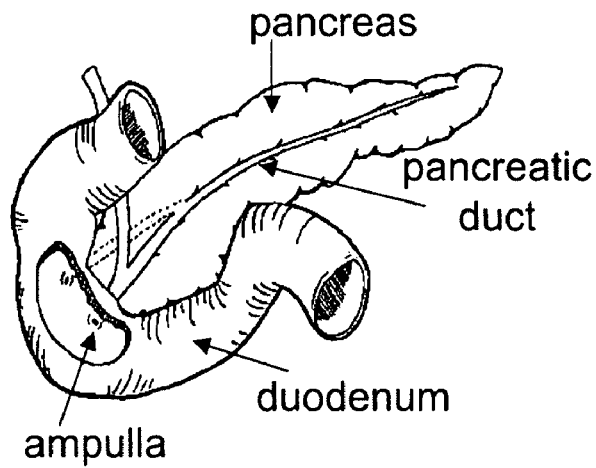
FIG. 3A illustrates the anatomy of the duodenal periampullary region and the pancreatic duct of the pancreas, according to one embodiment.

FIG. 3A illustrates the anatomy of the duodenal periampullary region and the pancreatic duct of the pancreas, according to one embodiment.

Interrogation of the pancreatic duct for pancreatic cancer screening introduces risk of acute pancreatitis. The adjacent periampullary duodenal mucosa can be accessed via existing upper endoscopy means and the examination of which presents a possibility to diagnose presence of pancreatic neoplasia without the potential risk of pancreatitis or other serious complications. Based on the field-effect, a neoplastic lesion in a particular tissue site such as the pancreas, can be detectable in the duodenal mucosa adjacent to the ampulla. The duodenal mucosa can be examined in vivo or ex vivo (e.g., from tissue biopsy samples obtained from endoscopy means).

Figure 3B:
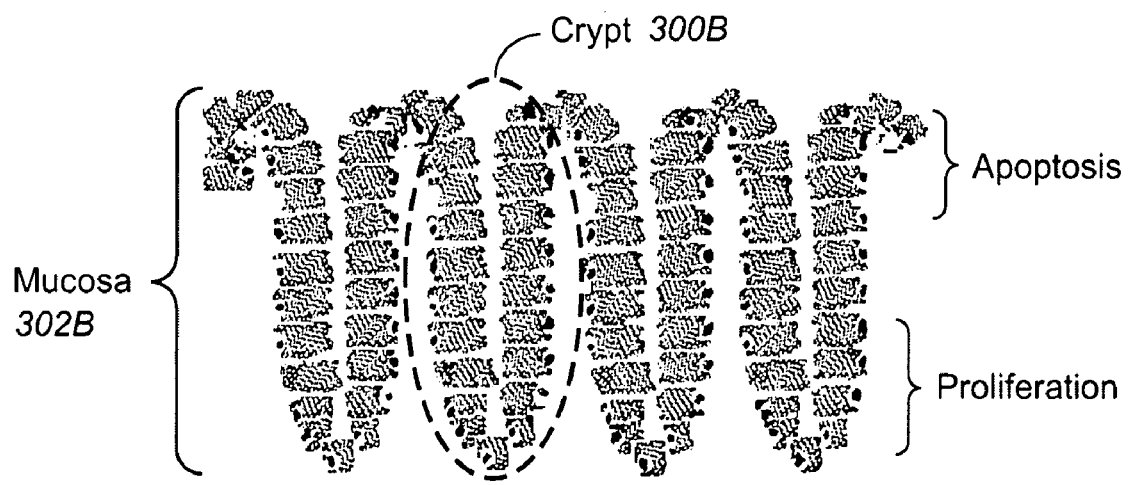
FIG. 3B is a plot illustrating the crypt: the major unit of the colonic mucosa, according to one embodiment.

FIG. 3B is a plot illustrating the crypt 300B: a major unit of the colonic mucosa 302B, according to one embodiment.

The epithelial cells can have distinct cell activities at various depths. A typical depth of a colonic crypt can be 70-90 μm. In adenomatous/carcinomous colonic mucosa, the apoptotic activity can be reduced in the base of the crypt while the proliferative activity is increased in the lumenal surface of the colon. The cells that are initially involved in neoplastic transformations are located in a specific area of the crypt: the base of the crypt is known as the location for initiation of colon carcinogenesis. Similar considerations apply to most other types of epithelia, including stratified squamous epithelium (e.g., the epithelium of uterine cervix, oral cavity, etc.).

Light scattering in biological tissue has been of great interest for tissue characterization and diagnosis. Results obtained by a number of investigators have illustrated that light scattering can provide diagnostically valuable information about tissue structure and composition. The most superficial tissue layer (i.e., the epithelium) is the origin of nearly 90% of human cancers and the epithelial cells are the first affected in carcinogenesis. Thus obtaining diagnostic information from superficial tissue can be crucial to the early diagnosis of epithelial precancerous lesions.

Differentiation between photons whose paths are limited to a superficial tissue layer and those traveling longer paths extending deep into the tissue requires specialized techniques, because the dominant portion of the light returned from the tissue is scattered multiple times from depths up to several $l_s^*$. Time-gating techniques use early-arriving photons to eliminate long-traveling photons. Polarization gating has been successfully used to distinguish between single and multiple scattering based on the depolarizing effect of multiple scattering.

The spectral analysis of the polarized component can be further used to obtain quantitative information about the morphology of superficial epithelial cells and to achieve imaging of superficial tissue.

LEBS enables the analysis of tissue organization at scales otherwise inaccessible to conventional microscopic or imaging techniques and ranging for a few tens of nanometers (below the resolution of optical microscopy used for histological analysis of tissue structure) to microns. Thus LEBS has enabled gathering of unattainable quantitative information about nano/microscale tissue architecture in situ.

For example, it has been demonstrated in animals studies that LEBS spectroscopy is shown as a new technique for depth-selective tissue diagnosis and can be used to identify pre-neoplastic changes in the initial stages of carcinogenesis, far earlier than is currently possible using any histological, molecular, or genetic means. Thus, LEBS can be used to detect early precancerous lesions earlier than it is feasible using other available techniques. Furthermore, data demonstrating that LEBS may allow screening for colon cancer without colonoscopy has been established.

Low-Coherence Enhanced Backscattering Optical Markers

Spectral Slope

Spectral behavior of $I_{EBS}(k)$ depends on the size distribution of light-scattering structures. Generally, $I_{EBS}(k)$ is a declining function of wavelength, and the steepness of the decline can be related to the relative portion of structures of different sizes. Larger structures that approach micron and supra-micron sizes (i.e., cellular organelles, etc.) tend to reduce the steepness of the change of $I_{EBS}(k)$ over wavelength, whereas smaller scatterers (sizes as small as ~20 nm) tend to increase the steepness of $I_{EBS}(k)$ over wavelength.

To characterize $I_{EBS}(k)$ with a single variable, linear fits to $I_{EBS}(k)$ can be obtained using linear regression from 530 to 640 nm. The absolute value of the linear coefficient of the fit is referred to as the "LEBS spectral slope" and quantifies the dependence of an LEBS spectrum on wavelength.

Spectral Exponential

Similarly $I_{EBS}(k)$ can vary based on the exponential power of the wavelength. For example $I_{EBS}(k) \propto \lambda^{-\alpha}$, where α is referred to as the spectral exponential.

Autocorrelation Decay Rate

Generally, the spectral profile $I_{EBS}(\lambda)$ of LEBS peak is a declining oscillatory function of wavelength, including high-frequency oscillatory features $I_{EBS}^{high}(\lambda)$ on top of the low-frequency declining profile $I_{EBS}^{low}(\lambda)$. The high-frequency oscillation $I_{EBS}^{high}(\lambda)$ can be linked to the tissue nano/microstructural refractive index variation. The high-frequency component can be extracted by subtracting the low-frequency profile from LEBS spectrum $I_{EBS}(\lambda)$.

The autocorrelation function of the LEBS spectra was calculated from $C(\Delta k)=\langle I_{EBS}^{high}(k)I_{EBS}^{high}(k+\Delta k)\rangle / \langle I_{EBS}^{high}(k)I_{EBS}^{high}(k)\rangle$ where k is the wave-number ($k=2\pi/\lambda$). The autocorrelation of the LEBS spectra can reveal the degree of refractive index fluctuations in tissue micro-architecture of the optically examined sample. It is determined from LEBS data that, $C_A(\Delta k) \propto \exp(-\Delta k^2 D)$, which is characteristic of random mesoscopic systems where D is the decay rate. Additionally, $D \propto (\delta n^2 L_C/L_t)^{-1} \lambda^2$, where $\delta n^2$ is the variance of refractive index fluctuations, $L_C$ is the refractive index correlation length, and $L_t$ is the temporal coherence length of illumination. It was determined that the decay rate D was decreased in patients with adenoma or carcinomas (p<0.016).

Peak Width and Enhancement Factor

The low coherence enhanced backscattering peak at the center of angular distribution (i.e., LEBS peak) can be determined in both angular and spectral dimensions. The angular profile of LEBS peak $I_{LEBS}(\theta)$ can be used to calculate the full-width at half maximum and enhancement factor of the LEBS intensity. The width and the enhancement factor have been demonstrated to be sensitive to optical properties of tissue architecture, such as scattering coefficient and optical density. The peak width of LEBS can be characterized as the full-width at half maximum (e.g., FWHM) of the LEBS peak $I_{LEBS}(\theta)$ averaged within a predetermined wavelength range (e.g., from 620 to 670 nm). The enhancement factor is defined as the ratio of the LEBS peak intensity $I_{LEBS}(\theta=0°)$ to the incoherent baseline intensity $I_{BASE}(\theta)$ outside of the LEBS peak, which can be measured for larger angles of backscattering (e.g., $\Theta>3°$) for substantially similar wavelength ranges.

The spectral behavior of the LEBS signal primarily depends on the second-order scattering of weakly localized photons by tissue structures, which is a contrast mechanism that is not easily probed by other existing techniques. The spectrally resolved LEBS signals can be normalized as: $I_{EBS}(\theta,\lambda)=(I(\theta,\lambda)-I_{BASE}(\lambda))/I_{REF}(\lambda)$, where $I_{BASE}$ is the baseline (incoherent) intensity and $I_{REF}$ is the reference intensity collected from a reflectance standard (this normalization to account for the non-uniform spectrum of the incident light illumination and the spectral response of detection).

Fourier Transform of $I_{LEBS}(\theta)$

The Fourier transform of the angular profile of LEBS peak $I_{LEBS}(\theta)$ can be used to calculate the decay rate of the transform with respect to the independent Fourier variable. For example, the decay rate is $$\frac{d}{dr}P(r),$$

where $P(r)=FT\{I_{LEBS}(\theta)\}$.

The decay rate can be sensitive to optical properties of tissue architecture, such as scattering coefficient and optical density.

Principal Component Index.

In addition, principle component analysis (PCA) of LEBS spectra can be performed. The first two principal components (PC1 and PC2) were determined to accounted for ~99% of the data variance. In search for an LEBS marker based on PCA, the PC index (PCI) was defined as a linear combination of PC1 and PC2. In one set of data, PCI=PC1+5PC2 was determined to be the most significant. The PCI index was found to be significantly decreased at two weeks time point (p-value<0.02) and continued to progressively decrease over the course of the experiment (p-value<0.000001). The temporally progressive change in PCI indicates that it is not due to an acute side-effect of AOM.

The spectral behavior of the LEBS signal primarily depends on the second-order scattering of weakly localized photons by tissue structures, which is a contrast mechanism that is not easily probed by other existing techniques. The spectrally resolved LEBS signals can be normalized as: $I_{EBS}(\theta,\lambda)=(I(\theta,\lambda)-I_{BASE}(\lambda))/I_{REF}(\lambda)$, where $I_{BASE}$ is the baseline (incoherent) intensity and $I_{REF}$ is the reference intensity collected from a reflectance standard (this normalization to account for the non-uniform spectrum of the incident light illumination and the spectral response of detection).

Figure 4A:
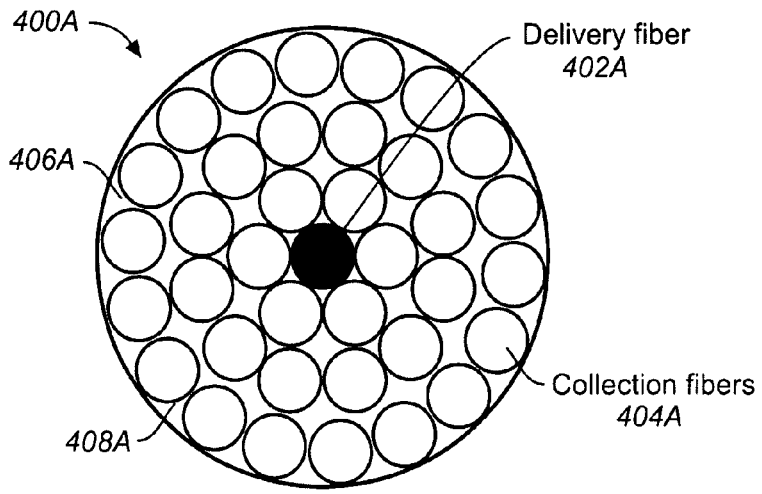
FIG. 4A is a cross sectional view of a probe having a plurality of optical fibers suited for ELF and/or LEBS spectroscopy, according to one embodiment.

FIG. 4A is a cross sectional of a probe 400A having a plurality of optical fibers suited for ELF and/or LEBS spectroscopy, according to one embodiment.

The probe 400A includes a delivery optical fiber 402A and a plurality of collection optical fibers 404A that surround the delivery optical fiber. In one embodiment, the probe is suitable to be inserted into an endoscope or a laparoscope. Multiple collection optical fibers enable collection of a broad set of angular components of the backscattering angle of backscattered light thus enabling LEBS spectroscopy. The relative positions of the delivery optical fiber and the collection optical fibers is not limited to what is shown. For example, the delivery fiber can be disposed towards the edge of the fiber rather than near the center. Projection of incident light at a small angle (e.g., 15 degrees) from the normal of the sample prevents specular reflection from masking the backscattered signal.

In one embodiment, the probe includes a polarizer 406A and another polarizer 408A coupled to the collection optical fibers to collect light polarized in different directions. As such, ELF signals can be recorded and epithelial characteristics of the imaged tissue can be determined when a polarizer is polarized in a direction substantially parallel to the incident light and the another polarizer is polarized in a direction substantially perpendicular to the incident light.

In one embodiment, more than one delivery optical fibers can be implemented in a probe. For example, spectroscopy signals can be obtained from imaging multiple tissue locations simultaneously with multiple optical delivery fibers. Each delivery optical fiber can be coupled to different or the same light sources. Depending on the application, different wavelengths of light can be coupled to each delivery optical fiber or set of delivery optical fibers to image tissue of different anatomical regions.

Figure 4B:
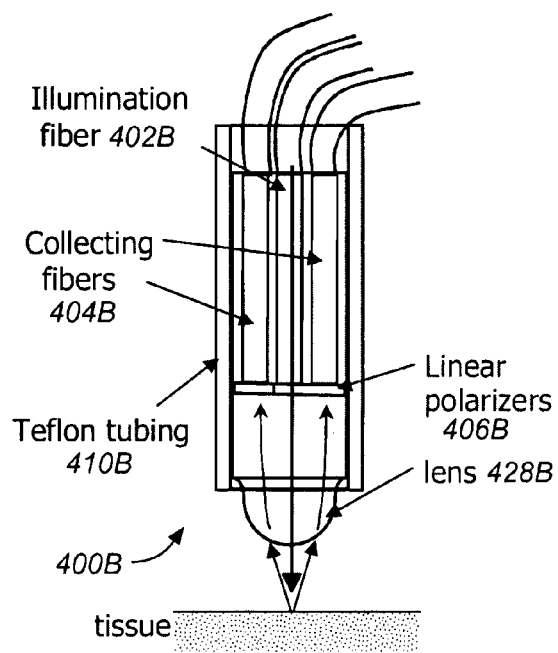
FIG. 4B is a side view of a probe suited for ELF and/or LEBS spectroscopy, according to one embodiment.

FIG. 4B is a side view of a probe 400B suited for ELF and/or LEBS spectroscopy, according to one embodiment.

The probe 400B includes a delivery optical fiber (illumination fiber) 402B and a set of collection optical fibers (collecting fibers) 404B enclosed in a tubing 410B (e.g., teflon). The side view also illustrates a set of polarizers 406B and a lens 408B coupled to a proximal end of the probe to deliver incident light to the tissue. In one embodiment, the tubing comprises material that is FDA approved for spectroscopy for medical purposes.

Figure 4C:
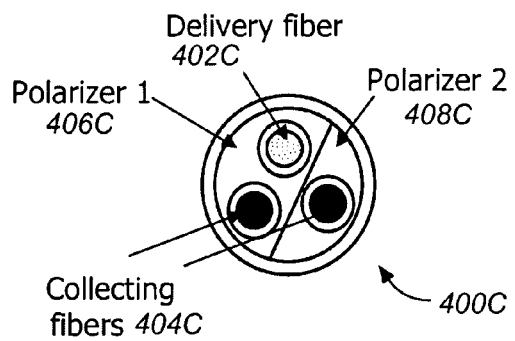
FIG. 4C is a cross sectional view of a probe having at least one delivery optical fiber and at least one collection optical fiber suited for ELF and/or LEBS spectroscopy, according to one embodiment.

FIG. 4C is a cross sectional of a probe 400C having at least one delivery optical fiber 402C and at least one collection optical fiber 404C suited for ELF and/or LEBS spectroscopy, according to one embodiment.

Probe 400C is a simplified version of probe 400A shown in FIG. 4A. By having a smaller number of collection optical fibers 404C, a smaller set of angular components of the backscattering angle of backscattered light can be collected. In one embodiment, the probe includes a polarizer 406C and 408C to collect polarization information about the backscattered light. For example, one of the polarizers can be oriented in a direction parallel to the incident light and the other polarizer can be polarized in a direction perpendicular to the incident light. Alternatively, other angles of polarization can be used with more or less numbers of polarizers as illustrated in the figure. Similar to the probe of FIG. 4A, more or less delivery optical fibers and collection optical fibers can be included without deviating from the scope of the disclosure.

Figure 5A:
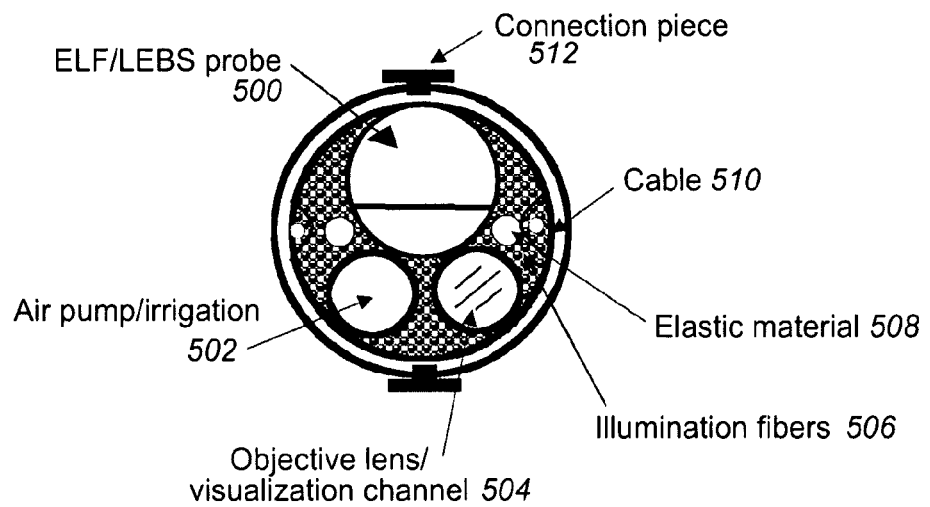
FIG. 5A is a cross-sectional view of the distal end of a scope having a probe suited for ELF and LEBS spectroscopy, according to one embodiment.

FIG. 5A is a cross-sectional view of the distal end of a scope having a probe suited for ELF and LEBS spectroscopy, according to one embodiment.

The objective of scope (e.g., rectoscope, colonoscope, endoscope, laparoscope) is to enable ELF/LEBS measurements in vivo, such as from the rectum facilitated by the visual inspection of rectal surface and suction/irrigation of the surface if necessary. The channel 502 is suited to deliver gaseous or liquid substance into the human body to cleanse the target object. For example, the channel is suited to deliver air and water. Multiple suction/irrigation channels may be incorporated if necessary.

The overall diameter of the scope can range from several millimeters to above 10 mm. In one embodiment, the scope (rectoscope) has two channels. The optical probe 500 (for LEBS and ELF spectroscopy) can be adapted to be inserted into one of the channels, while the other can be used for irrigation and suction. In one embodiment, to achieve tissue visualization, tissue is illuminated by an array of illumination fibers 506 and the magnified image is collected by the objective lens 504 and projected onto an LCD display. Components of the rectoscope is made from FDA approved materials. In one embodiment, more than one channels are used for optical probe insertion.

The scope is an example of an apparatus couple-able to a light source and a target object, to facilitate light transmission between the light source to the target object, includes a probe to emit incident light that is partially coherent light obtained from the light source onto the target object and to receive interacted light.

Figure 5B:
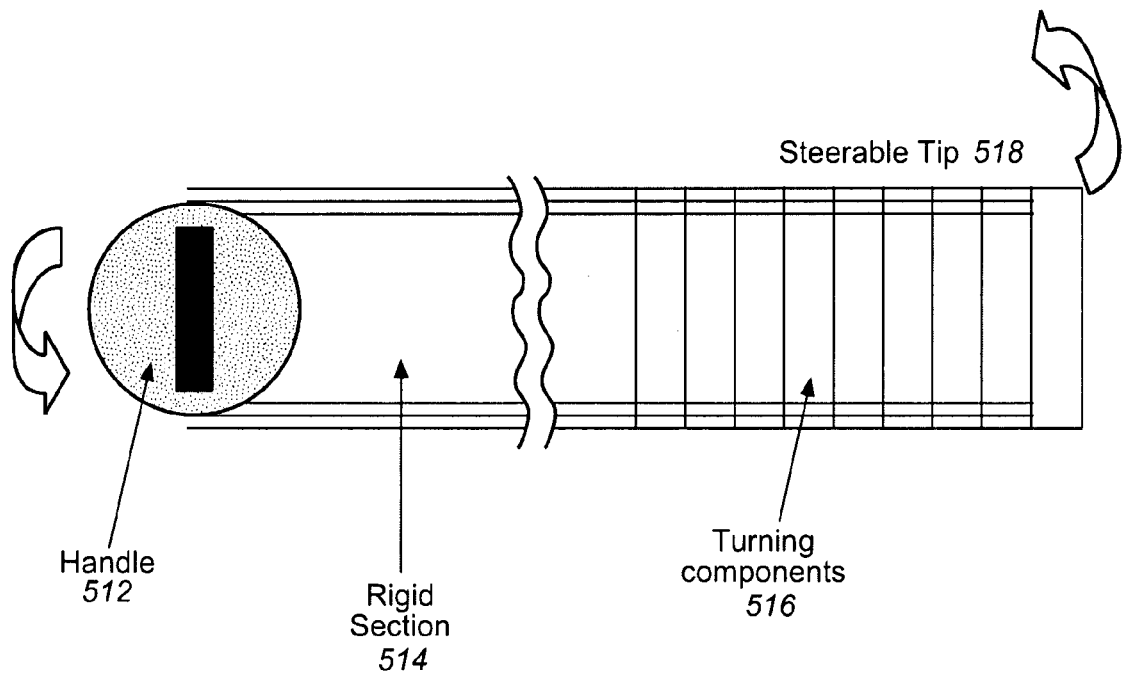
FIG. 5B is a cross-sectional view illustrating the steering mechanism of the scope, according to one embodiment.

FIG. 5B is a cross-sectional view illustrating the steering mechanism of the scope, according to one embodiment.

The distal end of the scope (i.e., the closest to tissue) has a rigid portion 514 and a flexible portion 516-518. The flexing mechanism implemented can be similar to one used in conventional endoscopes to enable the user to flex the tip of the scope by turning the handle 512, for example. In one embodiment, the scope is guided by two stainless steel cables along length of the scope at its sides. These cables can control the motion of the scope at the tip assisted by elastic rods running through the length of the tube, which allows the tube to easily restore its original shape.

The tip of the rectoscope is made of smaller components that inter-connect at the top and bottom. This interconnection will allows for the 1D-motion of the tip. The motion is controlled by the handle 512 pulling the cables. The individual components positioned at the tip limit the curvature to prevent the breakage of the fiber-optic cables in the visualization and ELF/LEBS probe channels. In contrary to similar flexing mechanisms on the tips of endoscopes, which enable flexion in both directions, rectoscope design is simpler in that flexion in only one dimension is required. Because the rectoscope is inserted only up to the rectum, if necessary, the flexion in the other dimension can be provided by the operator by means of scope rotation. All that is needed that the tip of the probe be either bendable or pre-formed so as to facilitate the aiming of the probe tip at, or placement in actual contact with, the rectal mucosa.

Figure 5C:
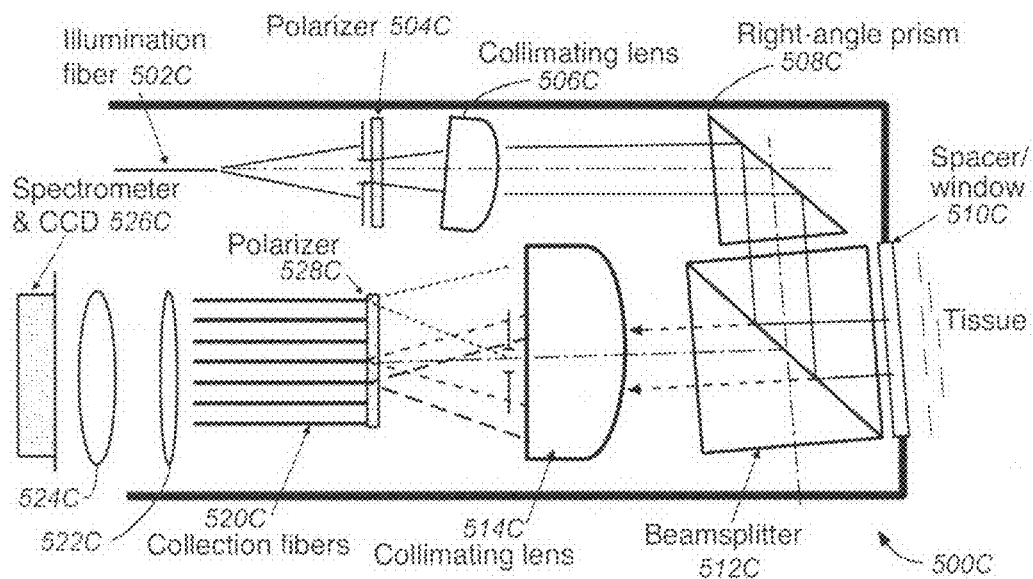
FIG. 5C is longitudinal view of the probe illustrating the schematic of the probe suited for ELF and LEBS spectroscopy according to one embodiment.

FIG. 5C is longitudinal view of the probe 500 illustrating a schematic of the probe suited for ELF and LEBS spectroscopy, according to one embodiment.

In one embodiment, the probe is to emit incident light that is partially coherent. The incident light can be obtained from a light source and is to be projected onto the target object and to receive interacted light. The interacted light can be backscattered light from illumination of the incident light on the target object. The probe 500 includes a delivery channel and a collection channel. The delivery channel includes at least one delivery optical fiber with a distal end portion couple-able to the light source and a proximal end portion suited to couple the incident light to the target object. In one embodiment, the delivery and collection channels are decoupled to avoid specular reflection and to enable measurement of LEBS peak for and around 0° backscattering angle. Light delivery may be achieved through a 50 μm optical fiber. In one embodiment, the delivery channel includes at least one delivery fiber (e.g., illumination fiber 502C).

In one embodiment, the length of spatial coherence is controlled by at least one of the degree of coherence of light coupled to the delivery fiber, properties of the fiber and the output (e.g., collimating) optics on the fiber tip. For example, the diameter of the at least one delivery optical fiber can be adjusted to determine the spatial coherence of the incident light. Since a larger fiber diameter supports more optical modes, the spatial coherence length of the output light decreases.

In addition, the numerical aperture of the at least one delivery optical fiber can be adjusted to determine the spatial coherence length of the incident light. For example, a larger numerical aperture decreases the spatial coherence length of the light output from the optical fiber.

The delivery channel can be suited to be coupled to a variety of light sources. For example, the light source can be a single broadband light source (e.g., an arc lamp that emits white light) with a smooth broad spectrum. Similarly, the light source can also be a white light emitting diode (WLED) to provide broadband illumination. In one embodiment, the light source is a combination of coherent light sources with different wavelengths. For example, the source can be a combination of lasers emitting at different wavelengths for providing effective coupling and high intensity of the incident light. Similarly, the light source may be a combination of LEDs that emit at different wavelengths.

By using semiconductor lighting devices (e.g., LEDs, lasers, etc.), sequential light pulses can be applied to the imaged target object. Different subsets of the LEDs and/or lasers can be switched on based on the desired illumination spectra since different applications may have different suitable illumination spectra due to specific anatomic properties. For example, tissues obtained from different anatomical regions may be more sensitive at different tissue depths. The ability to pulse different subsets of the semiconductor lighting devices (e.g., LED, lasers, etc.) can enable imaging different types of tissues for various applications with one probe.

In one embodiment, the spatial coherence of the light is controlled by a 4f-system with an aperture. An approximately 50 μm diameter delivery optical fiber is preferred to ensure adequate signal strength (LEBS was recorded) and the collimation of the light incident upon tissue (0.08°). However, in some embodiments, larger or smaller diameter delivery optical fibers can also be used. In one embodiment, a polarizer 504C and 518C positioned near the tip of the probe linearly polarizes the incident light as well as analyzes the polarization of the scattered light. Further, the incident light can be deflected by a micro-mirror or a micro-prism 508C and delivered onto a tissue surface.

The probe can further include a collection channel having a first collection optical fiber suited to collect substantially co-polarized backscattered light and a second collection optical fiber suited to collect substantially cross-polarized backscattered light. The substantially co-polarized backscattered light is polarized in a direction substantially parallel to the incident light and the substantially cross-polarized backscattered light is polarized in a direction substantially perpendicular to the incident light. In one embodiment, the first and second collection optical fibers are polarization-maintaining fibers.

The first collection optical fiber and the second optical fiber each having a proximal end portion to receive the light to be backscattered from illumination of the partially coherent light on the target object, and a distal end portion adapted to be coupled to a receiving end. The collection channel can be implemented with a bundle of optical fibers to sample a substantial portion of the angular data. This may be the ideal implementation when angular markers are important for analysis. In one embodiment, the collection channel is implemented with a smaller number of collection optical fibers useful when the spectral markers are more prominent.

The collection channel may be further coupled a micro-beam-splitter at a proximal end to divert the scattered light into the collection channel. The plurality of optical components may include a first polarizer optically coupled to at least one of the first and the second collection optical fibers to polarize the interacted light to be coupled to at least one of the first and the second collection optical fibers. In one embodiment, the backscattered light having the incident light polarization is selected by a polarizer coupled to at least one collection optical fiber. In one embodiment, the plurality of optical components further comprises a second polarizer optically coupled to at least one of the first and the second collection optical fibers to polarize the interacted light to be coupled to the at least one of the first and second collection optical fibers.

The first and second polarizers may be orthogonal to each other. In one embodiment, the first and second polarizers are at angles to each other that are different than 90 degrees and 45 degrees. In one embodiment, the polarizers can allow for the adjustment of polarization of at least one of the incident light and the interacted light. A polarizer can be the same polarizer 504C used to polarize the incident light. In one embodiment, the polarizer to select a particular polarization of the backscattered light that is different from the polarization of the incident light.

The probe may further include a plurality of optical components optically coupled to the proximal end portion of one or more of the at least one delivery optical fiber, the first collection optical fiber and the second collection optical fiber. In one embodiment, one or more of the plurality of optical components are optically coupled to the proximal end portion of the at least one delivery fiber to collimate the incident light. The optical components can be adjustably positioned at the proximal end portion of the at least one delivery optical fiber to vary the spatial coherence length of the incident light.

Furthermore, one or more of the plurality of optical components may be utilized to collimate the incident light. For example, the plurality of optical component includes at least one of a lens and an aperture. In one embodiment, at least one of the positions of the lens and the aperture are adjustable to vary a spatial coherence length of the partially coherent light to be projected on the target object.

In one embodiment, the plurality of optical components comprises a two lens 4-f system and an aperture disposed substantially in a common focal plane of the two lenses. The lens can be disposed substantially one focal length from the second end of the at least one optical fiber of the delivery channel and the collection channel. Substantially one focal length can be one focal length, greater than one focal length, or less than one focal length.

In one embodiment, the lens is to focus the backscattered light on the at least one collection optical fiber based on at least one angular component of backscattering angle of the backscattered light. A second lens may be optically coupled to the proximal end portion of the at least one collection optical fiber to focus the backscattered light on the at least one collection optical fiber based on the at least one angular component of the backscattering angle of the backscattered light. In one embodiment, the proximal end portion of the at least one collection optical fiber is optically coupled to one or more of the lens, the second lens, and a polarizer to project an angular distribution of the backscattered light on the spectrograph.

In one embodiment, a lens is positioned substantially a focal distance from the tips of the collection optical fibers. This lens can focus light backscattered from a sample onto different collection optical fibers based on the angle of backscattering. The lens can be at least one of a Fourier lens, a ball lens, a graded refractive index lens, an aspheric lens, a cylindrical lens, an aspherical lens, a positive lens, a convex-convex lens, and plano-convex lens. In one embodiment, the aspherical lens is preferred as it provides improved probe performance.

As discussed above, the number of collection optical fibers in the collection channel may vary depending on the application. For example, when a higher angular resolution is applicable, an imaging fiber bundle (e.g., probe 400A of FIG. 4A) can be used. Thus, the large number of collection optical fibers can enable measurement of the angular distribution of the backscattered light as well as its spectral composition for any given angle of scattering within this range.

Thus, the probe can collect the backscattered light from the imaged tissue as a function of scattering angle and deliver it to the imaging spectrometer coupled to an imaging device (e.g., CCD, photodetector, etc.). In one embodiment, the receiving end includes at least one of a spectrograph and a light detector. The spectrograph can be coupled to the light detector (e.g., CCD, photodetector) such that different spectral components of light can be recorded by the light detector thus resulting in a high spectral resolution of the collected optical data.

In one embodiment, the spectral information is acquired via sequential pulsing of the light source rather than the spectrometer. For example, semiconductor light devices (e.g., LED, lasers) can be sequentially pulsed in time at specific wavelengths. Thus, the detector can be gated in time to obtain snapshots that correspond to the wavelength of light that was pulse at a particular time The probe enables measurement of the angular components of the backscattering angles of the backscattered light as well as its spectral composition for an angle of scattering. In one embodiment, the receiving end includes multiple single-channel spectrometers to sample the LEBS spectra at discrete angular components. Each single-channel spectrometer can collect the backscattered light backscattered at a particular angle or a particular range of angles. The angular data to be obtained is based on the number of the channel spectrometers and/or the position of the channel spectrometers. The angle resolution that can be attained is based on the number of channel spectrometers.

In one embodiment, the receiving end includes a filter to sample the LEBS data at different wavelengths. The filter can be one or more of a tunable filter (e.g., accousto-optics), filter wheel, and dichroics. The filters can be used with a CCD (where all angles are measured) and/or a small number of detectors (e.g., photo-detectors, single channel spectrometers) where a discrete sample of angular components are measured.

Further, components of the probe can be made from FDA approved materials.

Figure 5D:
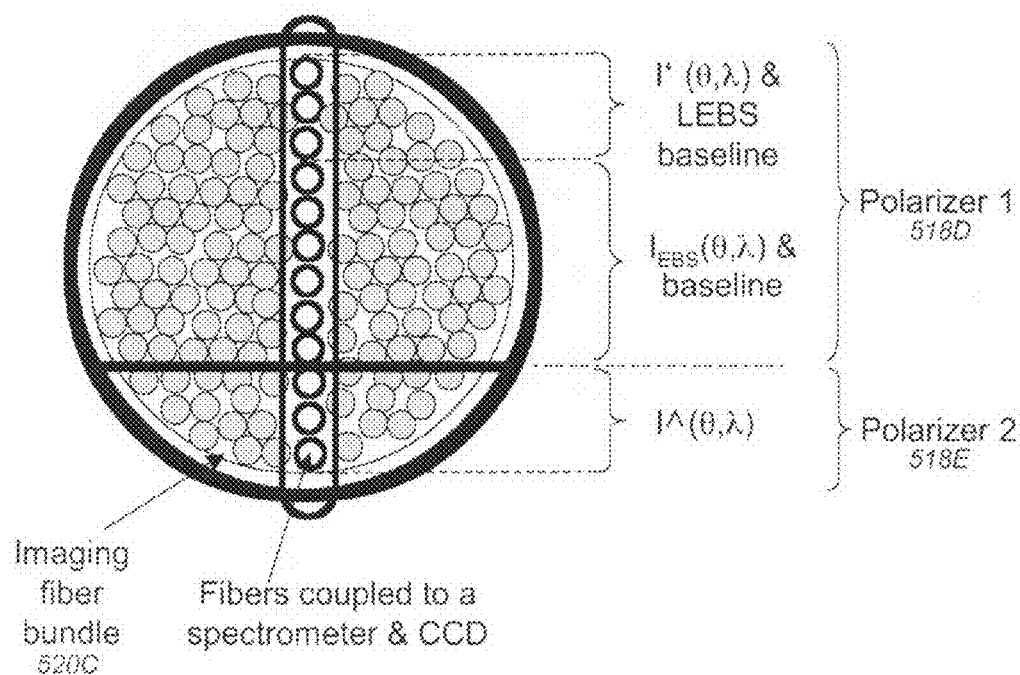
FIG. 5D is cross-sectional view of the probe having a plurality of collection and delivery optical fibers suited for ELF and LEBS spectroscopy according to one embodiment.

FIG. 5D is cross-sectional view of the probe 500 having a plurality of collection and delivery optical fibers suited for ELF and LEBS spectroscopy according to one embodiment.

According to one embodiment, to record ELF signals, at least one of the collection optical fibers is covered with a thin-film polarizer 518E oriented orthogonally to the polarizer (e.g., polarizer 518D) that polarizes the incident and LEBS signal. Thus, the collection optical fibers to receive ELF signals can receive light polarized substantially orthogonally to the direction of polarization of the incident light. These fibers can also be coupled into an imaging spectrograph and an imaging device (e.g., CCD). The difference between co- and cross-polarized signals can provide spectral ELF information.

Figure 6A:
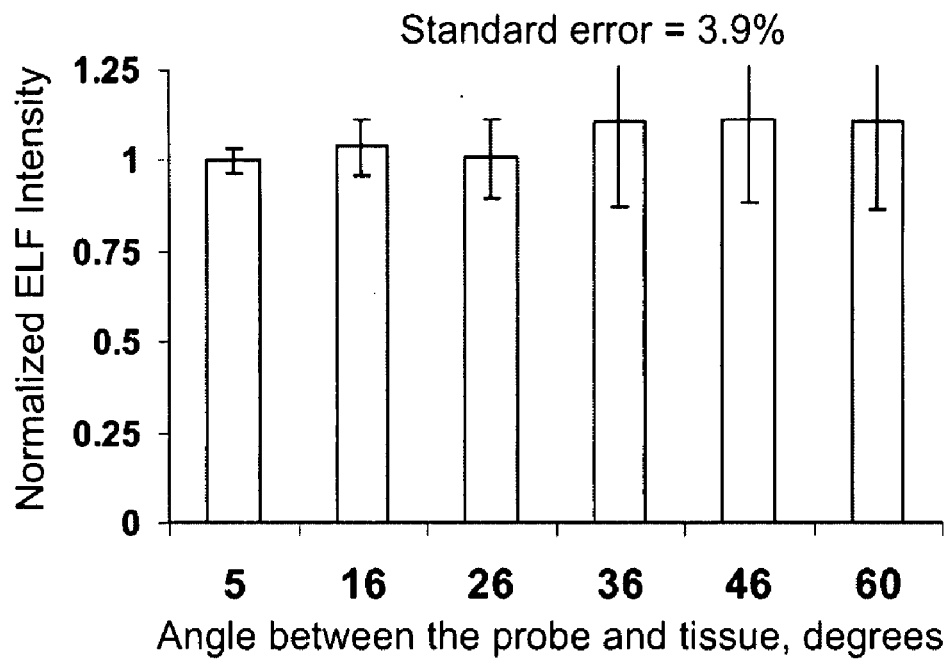
FIG. 6A is a bar diagram illustrating the dependence of the ELF intensity on an angle between an ELF probe and the imaged tissue, according to one embodiment.

FIG. 6A is a bar diagram illustrating the dependence of the ELF intensity on an angle between an ELF probe and the imaged tissue, according to one embodiment.

Figure 6B:
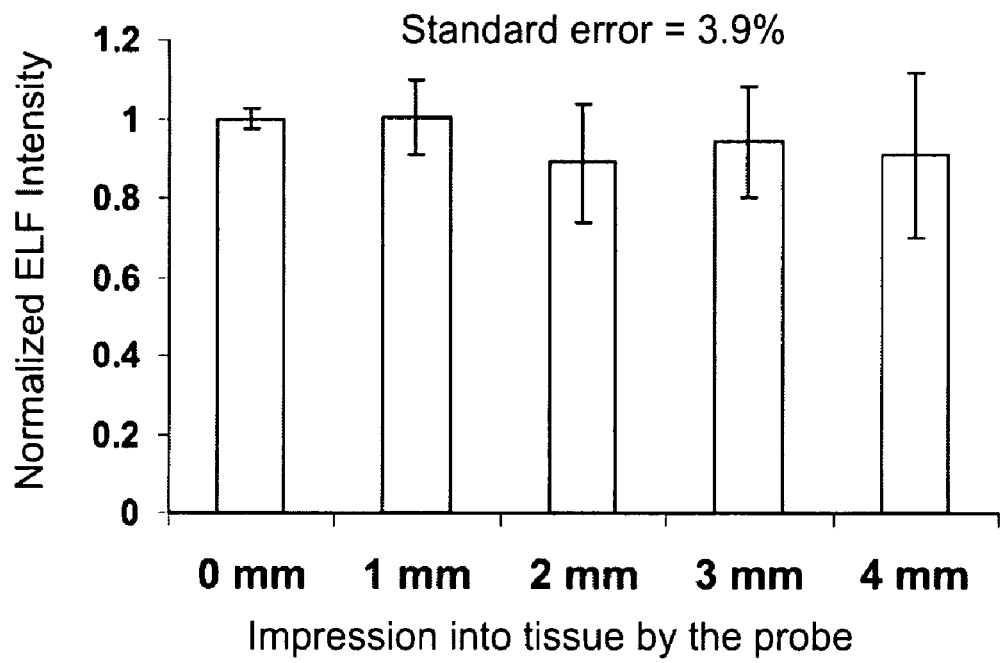
FIG. 6B is a bar diagram illustrating the dependence of the ELF intensity on the pressure exerted by the ELF probe on the tissue, according to one embodiment.

FIG. 6B is a bar diagram is a bar diagram illustrating the dependence of the ELF intensity on the pressure exerted by the ELF probe on the tissue, according to one embodiment.

Since the probe is to be used in vivo, the optical signals generated from the probe should be relatively reproducible and should not depend on the operator. Thus, the dependence of the optical signals on the pressure exerted by the probe onto the tissue and the angle between the probe and the tissue surface can be determined. FIG. 6B shows the results of experiments performed on ex vivo tissue resection specimens (size >> illumination spot size). The data illustrates that the probe design ensures the repeatability of optical outputs independent of the angle between the probe and the examined tissue and the pressure exerted on the tissue by the probe.

The pressure can be determined by the depth of impression made by the probe during its contact with the tissue (it is a convenient measure of pressure, because it can be visualized and controlled by an operator taking probe measurements in vivo). Even for high impressions up to 4 mm, the ELF signal level was stable with less than 4% change compared to low impression depths. Further, in an in vivo study performed on 200 patients, it was determined by participating endoscopists that it is fairly easy to control the pressure exerted by the probe within 1 mm. As a function of the angle between the probe and tissue surface, the signal was stable (<4% change) for angles <60°.

FIG. 7A is an intensity plot of LEBS signals recorded from histologically and/or endoscopically normal tissue in the AOM-treated rat model and a control rat, according to one embodiment, according to one embodiment.

FIG. 7B-C are intensity plots of ELF signals recorded from histologically and/or endoscopically normal tissue in the AOM-treated rat model and a control rat, according to one embodiment.

The LEBS spectra and ELF signals are recorded from histologically and/or endoscopically and macroscopically normal-appearing rectal tissues of rat colons at an early stage of carcinogenesis (e.g., 2 weeks post-AOM treatment) and age-matched control animals (e.g., saline treated rats). As shown, the ELF/LEBS signals obtained from preneoplastic and control colonic tissues are noticeably different. The time point, for which this alteration of light scattering was detected (i.e. 2 weeks after AOM-treatment), currently precedes the development of ACF or any other currently known markers of colon carcinogenesis. In this early stage, neoplastic changes cannot be currently detected by means of any other biomarkers, for example, ACF and adenoma or carcinomas develop 4-12 and 20-30 weeks after the AOM injection, respectively.

This is reminiscent of the clinical scenario of examining the mucosa in the distal colon (i.e. close to the rectum) in order to establish the presence of the "field effect" and hence risk for neoplasms throughout the colon. Moreover, changes in ELF/LEBS signals were observed in essentially all tissue sites assessed by ELF/LEBS. This is consistent with the concept of the field effect.

Figure 8:
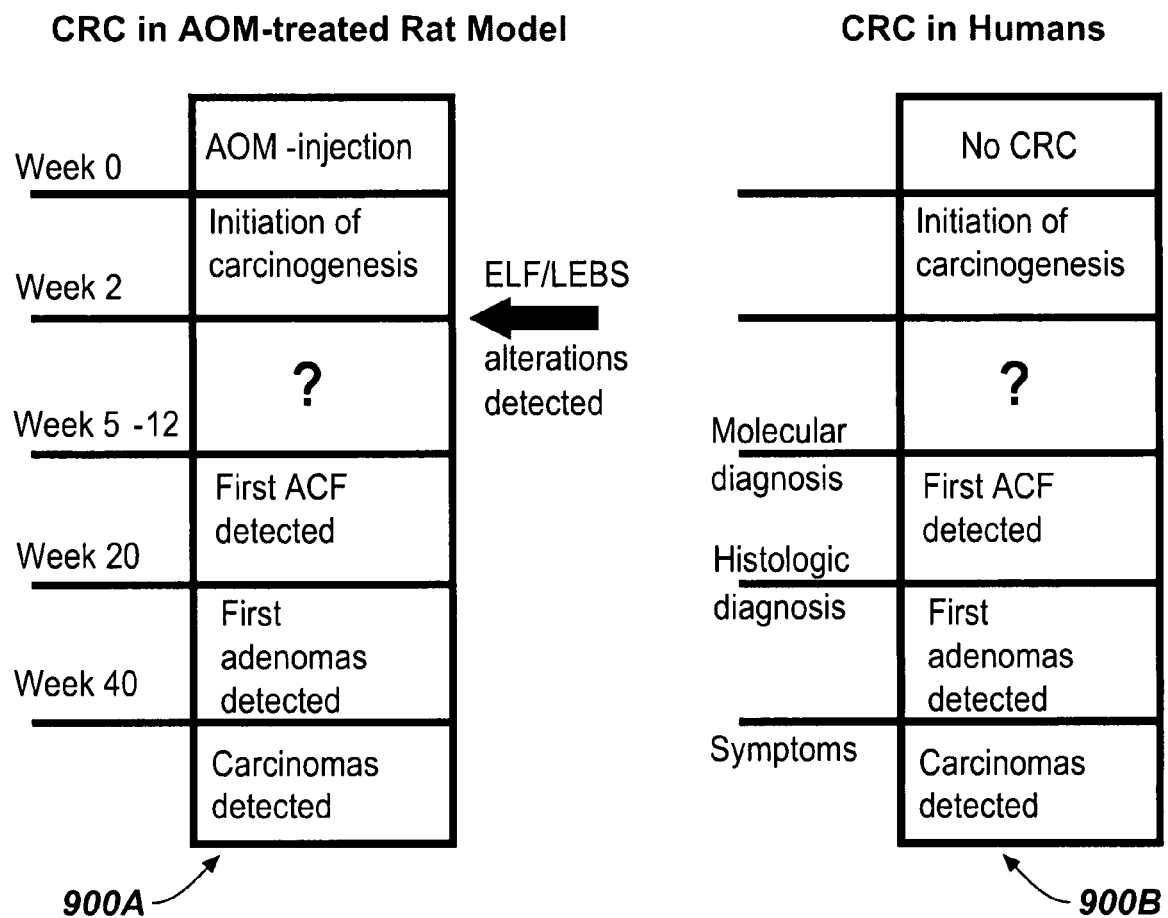
FIG. 8 illustrates the time course of colon carcinogenesis in the AOM-treated rat model and that in humans, according to one embodiment.

FIG. 8 illustrates the time course of colon carcinogenesis in the AOM-treated rat model and that in humans, according to one embodiment.

In azoxymethane (AOM)-treated rats, colon carcinogenesis progresses through similar steps as in humans. For example, the earliest detectable marker of colon carcinogenesis, aberrant crypt foci, are precursor lesions which are observed on the colonic mucosal surface in both the AOM-treated rat model and in humans. In AOM-treated rats, aberrant crypt foci develop in ~8-12 weeks after the AOM injection, adenoma or carcinomas can be observed in 20-30 weeks, and carcinomas develop after 40 weeks.

As in human colon carcinogenesis, end-stage lesions (e.g., tumors, 40 weeks after AOM injection) may be symptomatic. Earlier lesions (e.g., adenoma or carcinomas, >20 weeks post AOM treatment) may not lead to symptoms but can be detected histologically and/or endoscopically by means of microscopic examination of biopsy. Thus, the science of molecular biology may push the frontiers of cancer detection even earlier: Aberrant crypt foci can be detected as early as approximately 8 weeks after AOM treatment. However, no histological, molecular or genetic, markers have so far been discovered to allow diagnosis earlier than 4-12 weeks after the initiation of carcinogenesis.

Rats (e.g., Fisher rats) were randomized equally to groups that received either two weekly intraperitioneal injections of AOM (e.g., 15 mg/kg) or saline. Rats were fed standard chow and sacrificed at various time points after the second injection. Colons of the rats were removed, flushed with phosphate buffered saline, and immediately exposed to LEBS analysis to ensure that optical measurements were performed on fresh tissue.

Figure 9:
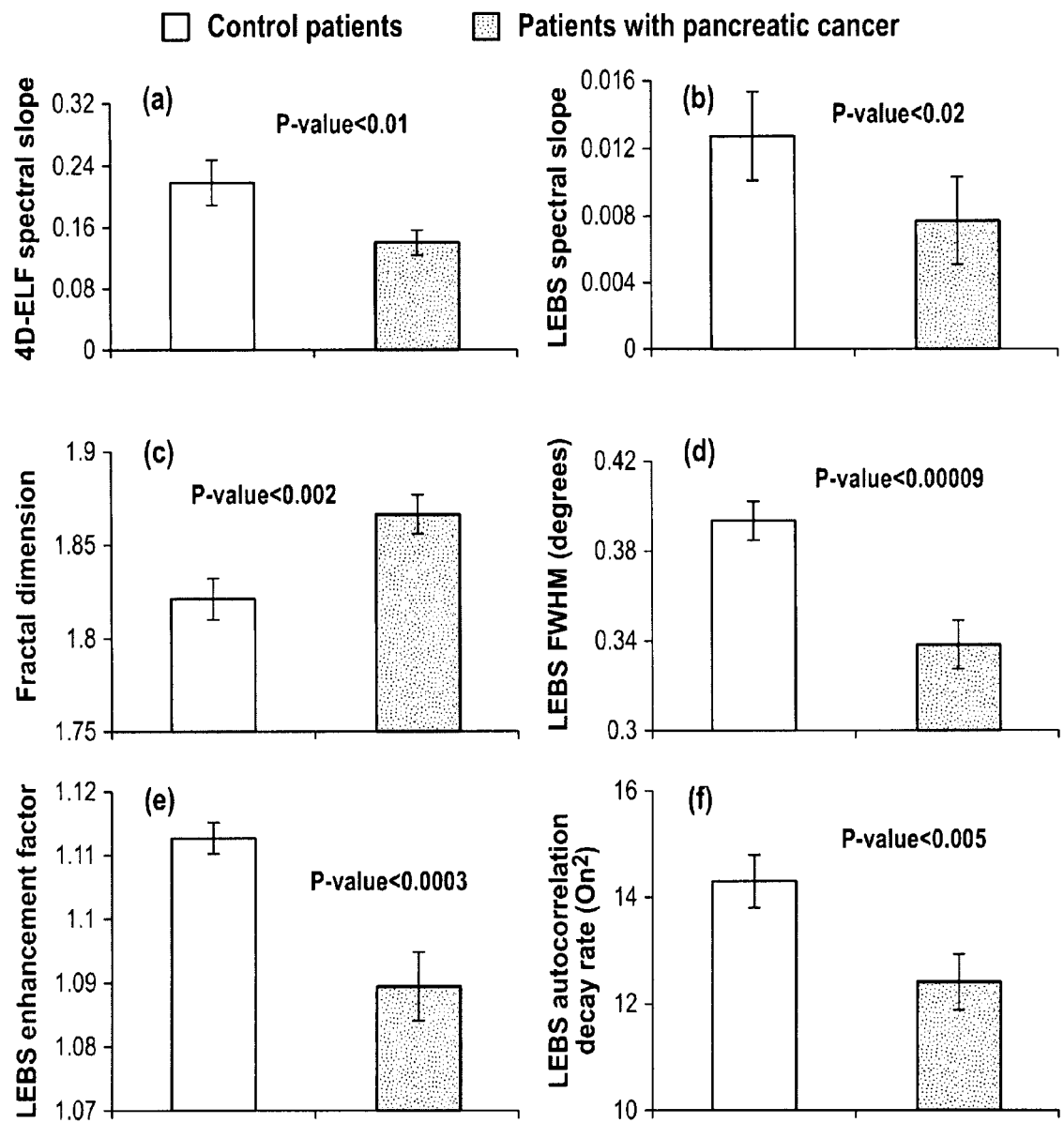
FIG. 9 is a series of plots illustrating ELF and LEBS optical markers obtained from tissue of the periampullary duodenum from patients with pancreatic cancer and control patients, according to one embodiment.

FIG. 9 is a series of plots illustrating ELF and LEBS optical markers obtained from tissue of the periampullary duodenum from patients with pancreatic cancer and control patients, according to one embodiment.

Biopsies can be taken from the histologically and/or endoscopically normal periampullary region in the duodenum in patients undergoing an upper endoscopic procedure who had pancreatic cancer (positive group) and those with no history of pancreatic disease or cancer (negative controls). The patients have pancreatic cancer confirmed by pathologic examination. The biopsied tissues are further analyzed by ELF and LEBS. After the optical reading, biopsied tissues were examined histo-pathologically to ensure that the tissues were histologically and/or endoscopically normal. By correlating the combined ELF and LEBS data with this diagnosis, a series of optical markers are determined to be diagnostic for pancreatic neoplasia.

As shown, the ELF spectral slope assessed from the periampullary mucosa is significantly lower for patients with pancreatic cancer as compared with control patients who were cancer-free (p-value<0.01). Similar analysis was performed on LEBS spectra $I_{LEBS}(\lambda)$ for depth of penetration 70 μm. As shown in the figure, the LEBS spectral slope obtained from the periampullary mucosa was also decreased in patients with pancreatic cancer (p-value<0.02).

In addition, the fractal dimension of tissue microarchitecture can be calculated from the Fourier transform $FT[\Delta I(\lambda=550\ nm,\theta,\phi=0°)](r)=C(r)$. The two-point mass density correlation function $C(r)$ quantifies the correlation between local tissue regions separated by distance r. Results indicate that, $C(r) \propto r^{D_f-3}$ for r from 1 to 50 μm, which is characteristic of a fractal-like tissue organization with fractal dimension $D_f$. As shown, $D_f$ obtained from the periampullary mucosa was elevated in patients with pancreatic cancer (p-value=0.002).

Furthermore, the angular width of the LEBS peak is decreased in pancreatic cancer patients (p-value=0.00009), which indicates an increase in the mean free path length of LEBS photons. The LEBS enhancement factor is also decreased in patients with pancreatic cancer (p-value=0.0003), which also suggests an increase in the mean free path length. The autocorrelation of LEBS spectra $C_A(\Delta k)=\int I_{EBS}(k)I_{EBS}(k+\Delta k)dk$, with k the wave number, reveals the degree of refractive index fluctuations in tissue microarchitecture. In the data obtained, $C_A(\Delta k) \propto \exp(-\Delta k^2 D)$, which is characteristic of many random mesoscopic systems with D referred to as the decay rate.

This exponential behavior of $C_A$ is characteristic of many random mesoscopic systems with D referred to as the decay rate. $D \propto (\delta n^2 L_C/L_t)^{-1}\lambda^2$, where $\delta n^2$ is the variance of the refractive index fluctuations within colonic mucosal tissue, $L_C$ is the refractive index correlation length, and $L_t$ is the temporal coherence length of illumination. D can be sensitive to essentially small length scales of refractive index fluctuations and, thus, concentration of tissue solids. As shown in the plot, it was determined that D was decreased in patients with pancreatic cancer.

FIG. 10 is a table showing performance characteristics of ELF and LEBS optical markers obtained from histologically and/or endoscopically normal duodenal periampullar mucosa for detection of pancreatic cancer, according to one embodiment.

The performance of the diagnosis obtained by combining all six optical markers had sensitivity and specificity >90%. This is one of the first demonstration of the feasibility of diagnosing pancreatic cancer without direct visualization of the pancreas. This performance level was attainable when six markers were included. For example, LEBS alone resulted in specificity and sensitivity of 74% and 84% indicating that both techniques provide complimentary diagnostic information.

Figure 11:
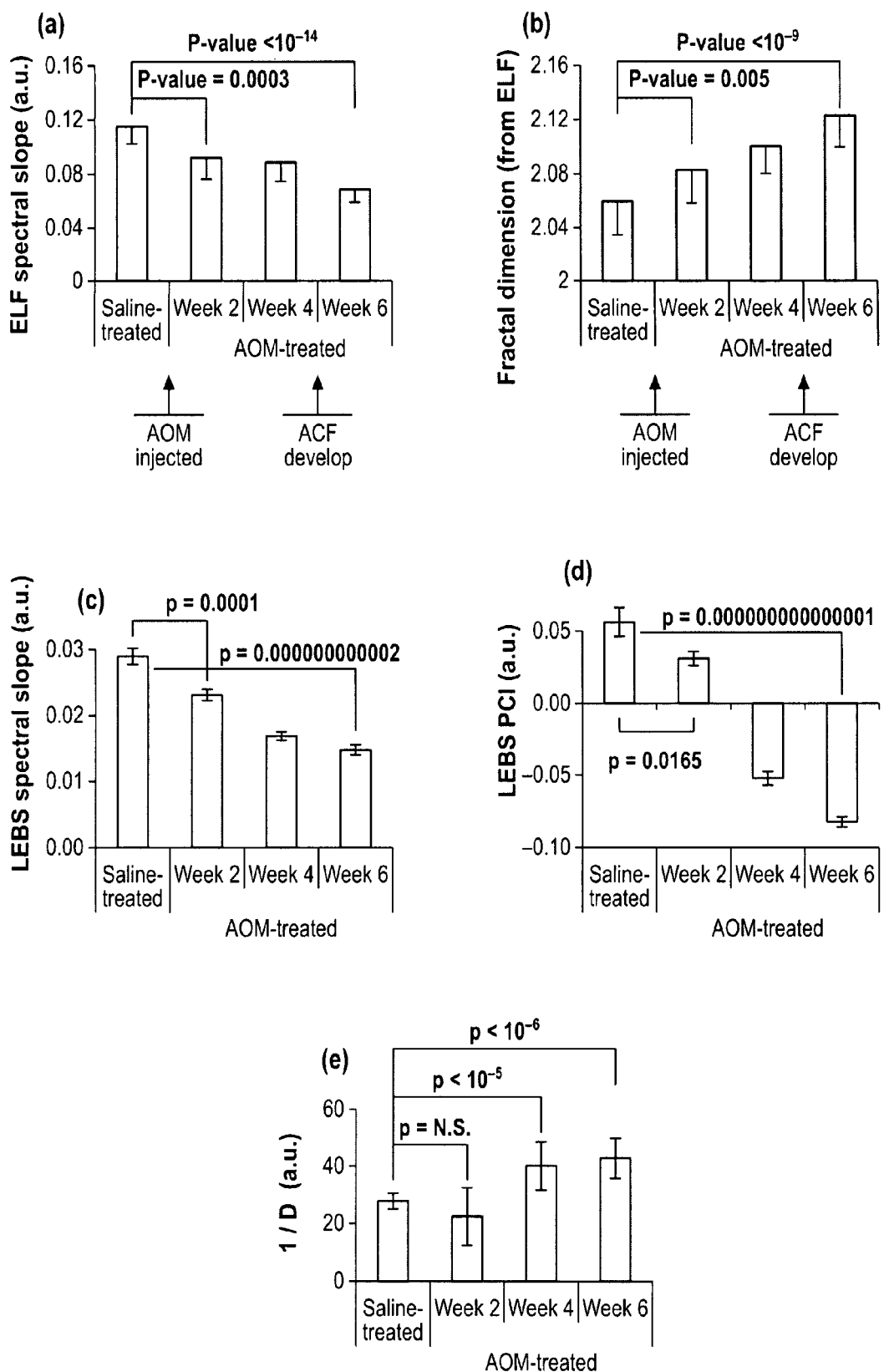
FIG. 11 is a series of plots illustrating ELF and LEBS optical markers obtained at various time periods after initiation of carcinogenesis in the AOM-treated rat model from normally appearing rectal or sigmoid colonic mucosa, according to one embodiment.

FIG. 11 is a series of plots illustrating ELF and LEBS optical markers obtained at various time periods after initiation of carcinogenesis in the AOM-treated rat model from normally appearing rectal or sigmoid colonic mucosa, according to one embodiment.

A number of ELF and LEBS markers are determined to be 1) significant for detection of early precancerous changes in the colons of the AOM-treated rats, 2) following the temporal progression of colon carcinogenesis, and 3) identifiable from histologically and/or endoscopically normally-appearing mucosa. Furthermore, the ELF/LEBS signals are obtained from histologically and/or endoscopically normal tissue from the rectum of either control or AOM-treated rats.

The optimal depth of penetration for which LEBS markers are more diagnostic can be determined. LEBS spectra corresponding to 30, 50 and 75 μm depths were assessed initially. Analysis of the LEBS data showed that 75 μm penetration depth provided diagnostically significant results and enables detection of colorectal carcinogenesis at an early time point (2 weeks after AOM injection). This depth approximately corresponds to the depth of colonic mucosa and several lines of evidence suggest that the base of the crypt is the location for initiation of colon carcinogenesis. (Signals recorded from deeper tissue are affected by hemoglobin absorption.)

At least five highly statistically significant markers can be identified for detection of colorectal carcinogenesis via ELF/LEBS optical examination.

1) ELF spectral slope can obtained as the absolute value of the linear coefficient of the linear fit to $\Delta I(\lambda,\theta,\phi)$ for fixed $\theta$ and $\phi$ (e.g., $\Delta I(\lambda,\theta,\phi)$ was integrated over $\theta$ for $\phi=0$, $\lambda=500$-650 nm). The spectral slope depends on the size distribution of scattering structure. For example, abundance of smaller (up to 40 nm) scatterers increases the spectral slope. Since the carcinogenic effects of AOM progress over time, it is to be expected that the magnitude of the alterations of the optical markers to increase over time.

As shown in FIG. 11, the ELF spectral slope progressively decreased at these early stages of CRC (2, 4 or 6 weeks post carcinogen injection). In the AOM-treated rats, the ELF spectral slope was noticeably decreased as early as 2 weeks after the carcinogen treatment (p-value<0.0003) and continued to decrease over the course of the experiment (ANOVA p-value<$10^{-10}$). Such progressive and statistically significant alteration of the spectral slope serves as a strong argument for the neoplastic relevance of this marker. The temporal progression of the spectral slope also indicates that the change is not due to an acute reaction of AOM or an unidentified nonspecific side-effect of the drug. This is further supported by the fact that AOM is removed from the body within one week after injection.

2) LEBS spectral slope. Similar analysis can be performed on LEBS spectra $I_{LEBS}(\lambda)$ for depth of penetration 75 μm. As shown in FIG. 11, in the AOM-treated rats, LEBS spectral slope was dramatically decreased as early as 2 weeks after the carcinogen treatment (p-value<0.00001) and continued progressively decreasing at later time points (ANOVA p-value<0.0001).

Fractal dimension of tissue microarchitecture can be calculated from the Fourier transform $FT[\Delta I(\lambda=550\ nm,\theta,\phi=0°)](r)=C(r)$. The two-point mass density correlation function $C(r)$ quantifies the correlation between local tissue regions separated by distance r. In the acquired data, $C(r) \propto r^{D_f-3}$ for r ranging from 1 to 50 μm, which is characteristic of a fractal-like tissue organization with fractal dimension $D_f$. As shown in FIG. 11, $D_f$ was elevated as early as 2 weeks post-AOM treatment (p=0.005) and continued to increase over time (ANOVA p=0.000000001).

4) Principal Component Index. Principle component analysis (PCA) of LEBS spectra can also be performed. It was determined that the first two principal components (PC1 and PC2) accounted for ~99% of the data variance. The PC index (PCI) is defined as a linear combination of PC1 and PC2 and PCI=PC1+5PC2 is determined to be the most significant. It is observed that PCI is significantly decreased at 2 weeks time point (p-value<0.02) and continued to progressively decrease over the course of the experiment (p-value<0.000001). The temporal progression of PCI indicates that the change of PCI is not due to an acute side-effect of AOM.

5) LEBS autocorrelation decay rate. Autocorrelation of LEBS spectra $C_A(\Delta k)=\int I_{EBS}(k)I_{EBS}(k+\Delta k)dk$, with k the wave-number, reveals the degree of refractive index fluctuations in tissue microarchitecture. $C_A$ is determined to follow exponential dependence on $\Delta k^2$, $C_A(\Delta k) \propto \exp(-\Delta k^2 D)$, with a good precision ($R^2$=0.98). This exponential behavior of $C_A$ is characteristic of many random mesoscopic systems with D referred to as the decay rate. $D \propto (\delta n^2 L_C/L_t)^{-1}\lambda^2$, where $\delta n^2$ is the variance of the refractive index fluctuations within colonic mucosal tissue, $L_C$ is the refractive index correlation length, and $L_t$ is the temporal coherence length of illumination.

Further, D is sensitive to arbitrary small length scales of refractive index fluctuations and, thus, concentration of tissue solids (up to 1 nm, as confirmed by our numerical FDTD experiments). It is determined that D was significantly increased at 4 weeks time point (p-value<$10^{-5}$) and continued to progressively increase following the progression of carcinogenesis (ANOVA p-value<0.01). This indicates progressive increase in tissue inhomogeneity in carcinogenesis.

FIG. 12 is a table showing performance characteristics of ELF and LEBS optical markers obtained from histologically and/or endoscopically normal rectal mucosa of rats, according to one embodiment.

Performance characteristics of rectal ELF/LEBS markers (AOM-treated rats vs. control rats) obtained from the histologically and/or endoscopically normal rectal mucosa of rats 2 weeks post AOM-treatment (i.e., time point when neoplastic changes cannot be detected using currently known histological/molecular means) and 6 weeks post AOM-treatment (i.e., pre-adenoma or carcinoma stage) are shown.

ELF/LEBS markers have been demonstrated to change significantly in the early stages of colon carcinogenesis: as early as 2 weeks after AOM-treatment, i.e. preceding the time points when the other conventional biomarkers of CRC can be currently detected. The relevance of these changes to carcinogenesis is further supported by the temporal progression.

Figure 13A:
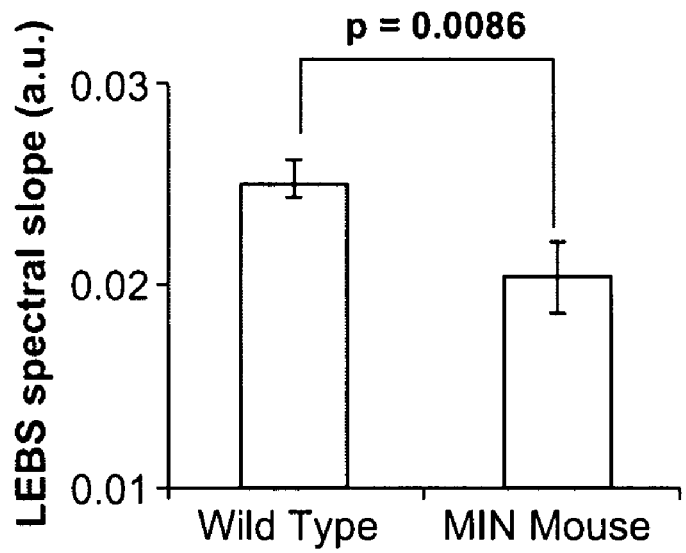
FIG. 13A is a plot illustrating changes in the LEBS spectral slope recorded from the uninvolved MIN mouse mucosa (distal small bowel) in the 6-week-old MIN mouse compared with age-matched mice that were wild type for APC loci, according to one embodiment.

A 100% sensitivity and specificity attained at a pre-adenoma or carcinoma stage of colon carcinogenesis indicates that a single reading would be sufficient to identify if a rat undergoing a neoplastic transformation by detecting the field effect. This capability is beyond any other previously described (both conventional and experimental) biomarkers, thus underscoring the promise of ELF/LEBS as a colon cancer screening tool. Furthermore, FIG. 12 illustrates that the combination of ELF and LEBS provides diagnosis superior to that of LEBS or ELF alone. This is expected, as ELF and LEBS provide complimentary information FIG. 13A is a plot illustrating changes in the LEBS spectral slope recorded from the uninvolved MIN mouse mucosa (distal small bowel) in the 6-week-old MIN mouse compared with age-matched mice that were wild type for APC loci, according to one embodiment.

Figure 13B:
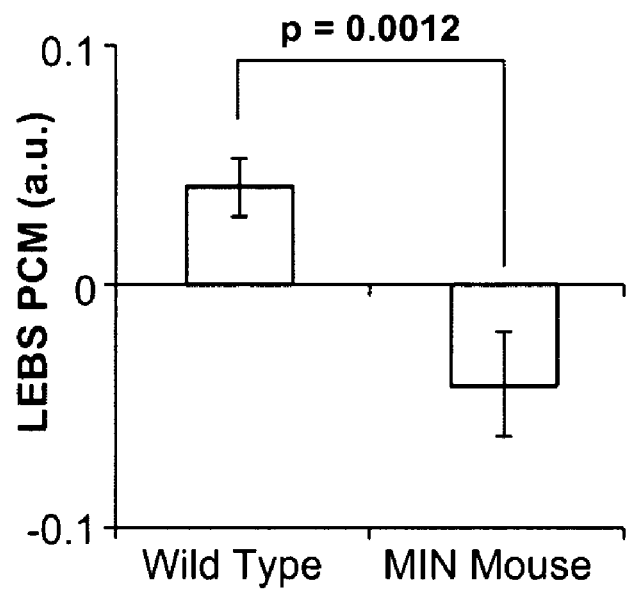
FIG. 13B is a plot illustrating changes in the LEBS principle component marker (PCM) recorded from the uninvolved MIN mouse mucosa (distal small bowel) in the 6-week-old MIN mouse when compared with age-matched mice that were wild type for APC loci, according to one embodiment.

FIG. 13B is a plot illustrating changes in the LEBS principle component marker (PCM) recorded from the uninvolved MIN mouse mucosa (distal small bowel) in the 6-week-old MIN mouse when compared with age-matched mice that were wild type for APC loci, according to one embodiment.

While the AOM-treated rat model is robust and well-validated, in order to ensure that the changes in ELF/LEBS signatures are not model-specific, the findings were repeated in an alternate model of intestinal carcinogenesis, the MIN mouse. The intestinal carcinogenesis model of the MIN mouse is a genetic model with a germline mutation in the adenomatous polyposis coli (APC), the initiating mutation in most sporadic colon carcinogenesis. The MIN mouse spontaneous develop intestinal adenoma or carcinomas starting at ages 9-10 weeks.

The ELF/LEBS signatures obtained from the MIN mice were compared with age-matched negative control C57BI mice. The control C57BI mice differ from the MIN mice in that they harbor a wild-type APC gene. Specifically, the intestinal mucosa can be evaluated at week 6 when the mucosa of preoplastic MIN mice is still histologically and/or endoscopically normal. The study involved n=18 animals (9 MIN and 9 control mice). For each animal, ELF/LEBS data were recorded for at least 20 different tissue sites spaced uniformly across the surface of the small bowel. It was found that the five ELF/LEBS markers that were significant for early colon carcinogenesis in the AOM-treated rats (see section C7), were also diagnostic for the pre-adenoma or carcinoma stage of the intestinal neoplasia in the MIN mice. FIG. 13 illustrates this by showing two examples: LEBS spectral slope and PCI. Both markers were significantly altered at this preneoplastic time point (p-values<0.01, sensitivity=88%, specificity=76%).

Figure 14:
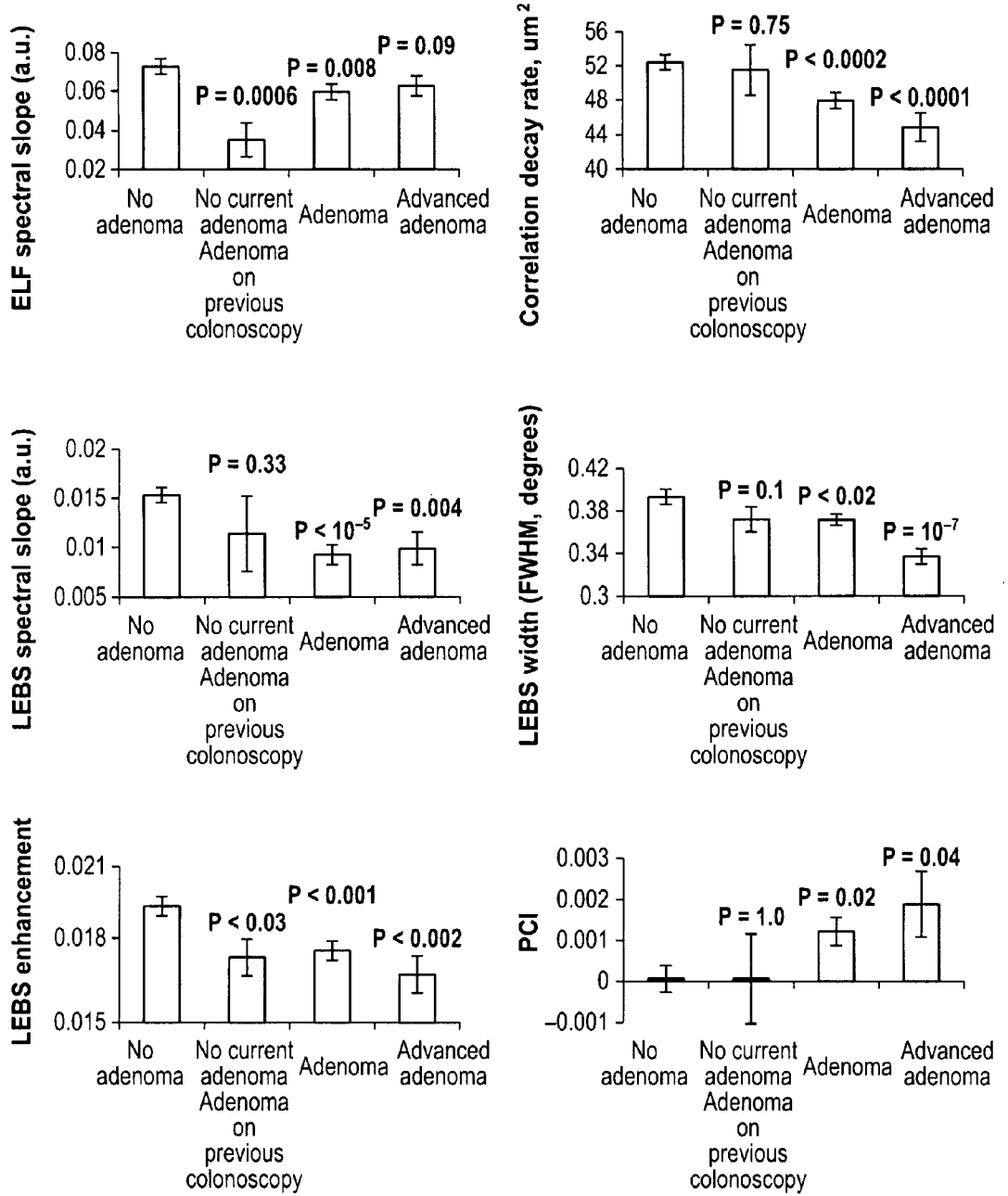
FIG. 14 is a series of plots illustrating a plurality of ELF and LEBS markers obtained from the rectum from patients with no adenoma or carcinoma, no current adenoma or carcinoma, and advanced adenoma or carcinoma, anywhere in the colon, according to one embodiment.

FIG. 14 is a series of plots illustrating a plurality of ELF and LEBS markers obtained from the rectum from patients with no adenoma or carcinoma, no current adenoma or carcinoma, adenoma or carcinoma, and advanced adenoma or carcinoma, anywhere in the colon, according to one embodiment.

The ELF/LEBS markers established in animal studies are determined to be significant in humans. Overall, at least six significant markers are determined to be significant: ELF spectral slope, LEBS spectral slope, correlation decay rate, PCI, the width of LEBS peak, and LEBS enhancement factor. The first four markers (spectral slopes, PCI and correlation decay) were previously discussed.

The LEBS peak width can be defined as a full width at half maximum (FWHM) of an LEBS peak averaged over wavelength. Decrease in the LEBS peak width indicates the increase in the average path length of LEBS photons. The LEBS enhancement factor was measured as the ratio of $1_{EBS}$ (0°) to the baseline intensity (also averaged over the spectral range). Decrease of the LEBS enhancement factor indicates the increase in the longest path length of the LEBS photons. As shown, ELF/LEBS signatures measured from histologically and/or endoscopically and colonoscopically normal-appearing rectal mucosa were significant for colonic adenoma or carcinomas in human. In addition, ELF/LEBS signatures can also be obtained from optical examination of tissue from the cecum, ascending colon, hepatic flexure, transverse colon, splenic flexure, descending colon, and/or sigmoid colon.

Figure 15:
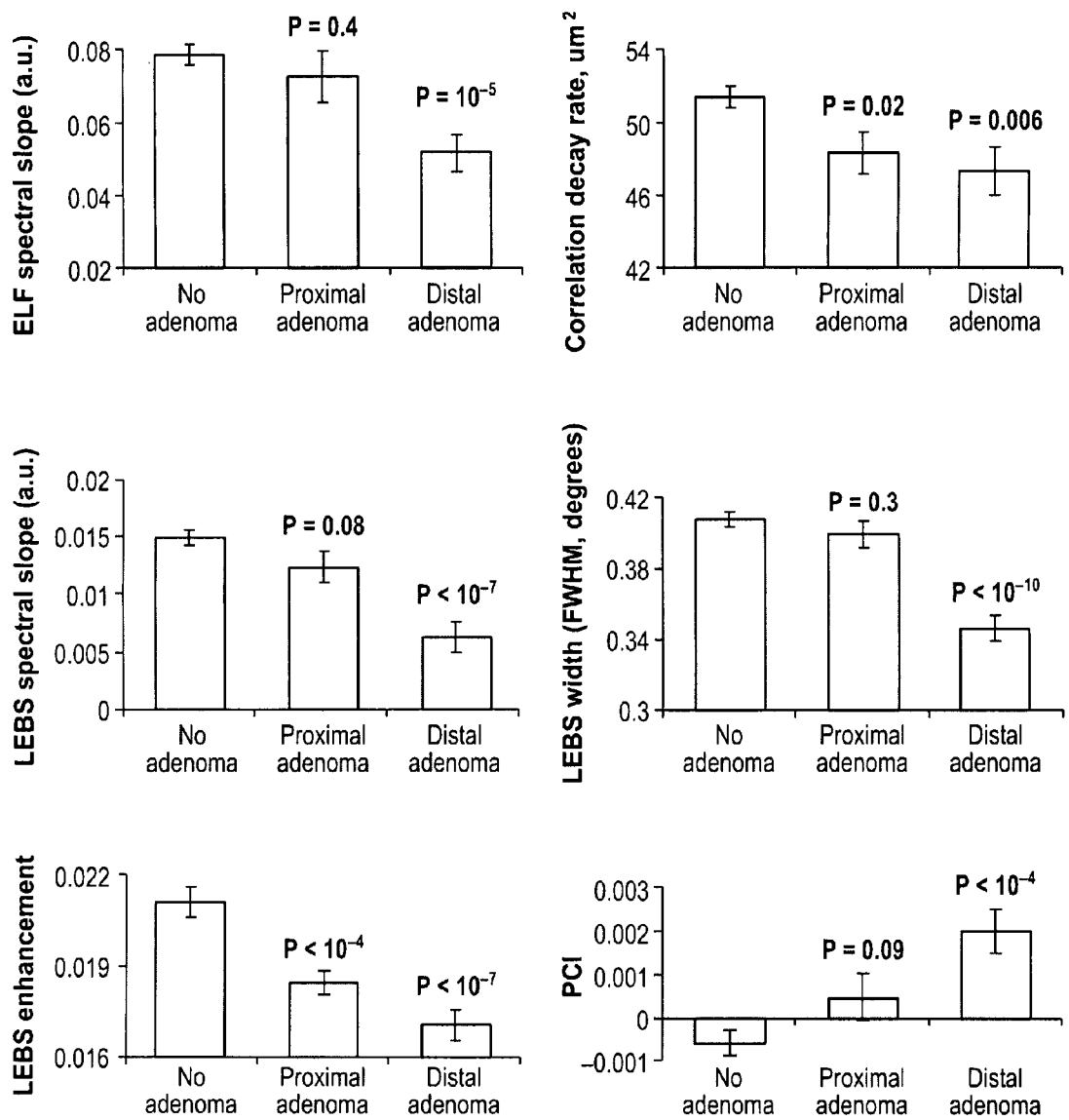
FIG. 15 is a series of plots illustrating a plurality of ELF and LEBS markers obtained from the rectum from patients with no adenoma or carcinoma, proximal adenoma or carcinoma, or distal adenoma or carcinoma, according to one embodiment.

FIG. 15 is a series of plots illustrating a plurality of ELF and LEBS markers obtained from the rectum from patients with no adenoma or carcinoma, proximal adenoma or carcinoma, or distal adenoma or carcinoma, according to one embodiment.

As illustrated in the plots, the alteration of ELF/LEBS markers in the rectum was observed for distal adenoma or carcinomas (rectum and sigmoid colon) and for proximal lesions (transverse and ascending colonic segments). In the data shown in FIG. 15, the number of patients without adenoma or carcinomas was n=105, patients with adenoma or carcinomas in the distal colon n=21, and patients with adenoma or carcinomas in the proximal colon n=23. The magnitude of the alteration of the optical markers was less pronounced for proximal adenoma or carcinomas—likely due to increased distance between these adenoma or carcinomas and the rectum. For example, while all six markers were significant for distal adenoma or carcinomas, two markers were significant for proximal adenoma or carcinomas and two were marginally significant (p<0.1). Higher p-values for proximal adenoma or carcinomas may in part be due to smaller n's.

ELF/LEBS Markers are not Affected by Benign Colonic Lesions

Figure 16:
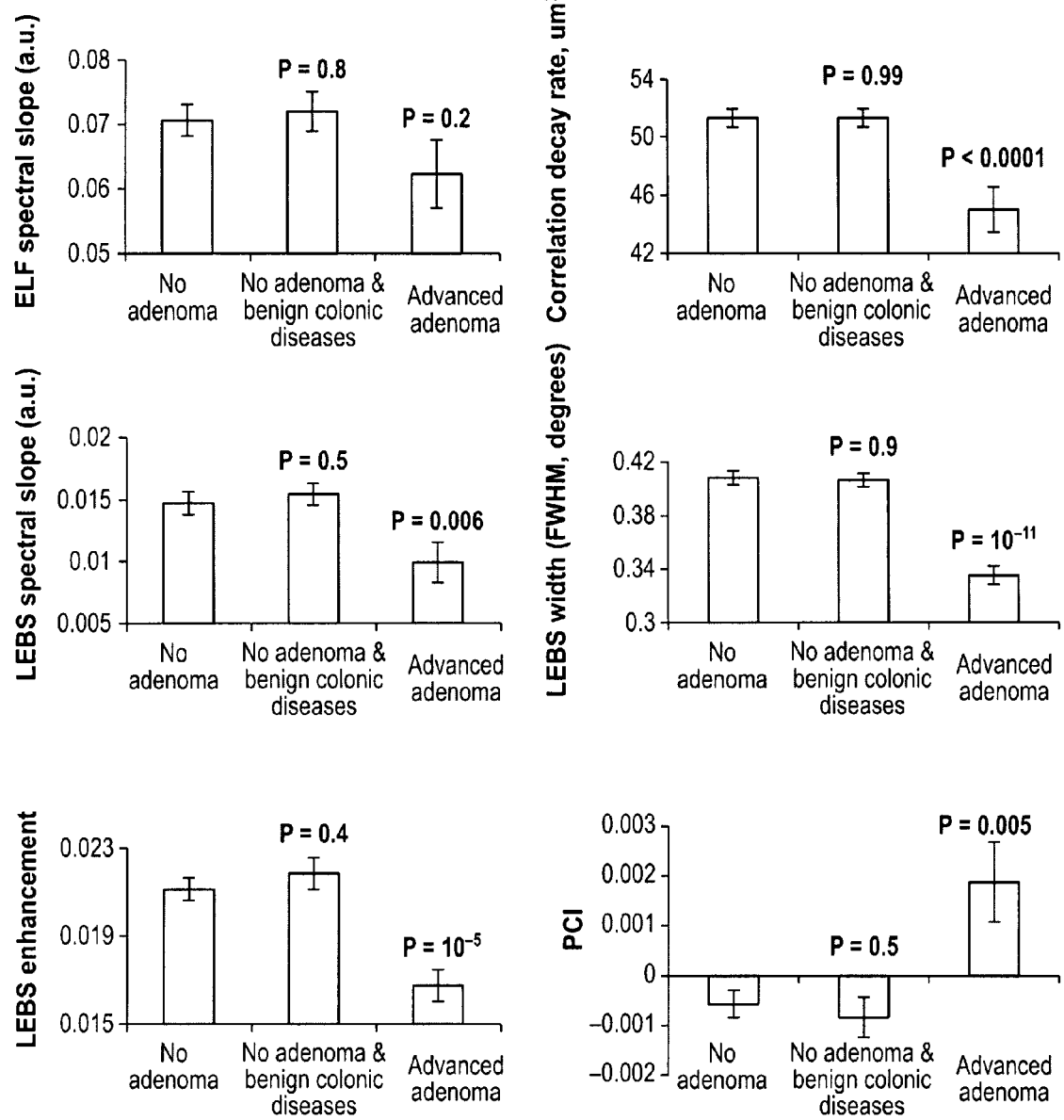
FIG. 16 is a series of plots illustrating a plurality of elastic light scattering and low coherence enhanced backscattering markers obtained from the rectum from patients with no adenoma or carcinoma, benign diseases, and advanced adenoma or carcinoma, according to one embodiment.

FIG. 16 is a series of plots illustrating a plurality of ELF and LEBS markers obtained from the rectum from patients with no adenoma or carcinoma, benign disease, and advanced adenoma or carcinoma, according to one embodiment.

There is no biological basis to assume hyperplastic polyps (the most prevalent benign colonic lesions) and colitis (less prevalent) may have an effect on the optical markers of the field effect: based on the available data, these diseases do not have the field. This can be confirmed using human data. Among the patients recruited for the study who were adenoma or carcinoma-free, 42 patients had no colonoscopic findings, 38 had diverticular disease, 24 had hyperplastic polyps, and 5 had colitis. As illustrated, neither diverticular disease, hyperplastic, polyps, or colitis had a significant effect on the ELF/LEBS markers. The results address a potential concern whether these benign conditions might be a source of false positives 4D-ELF/LEBS Diagnosis is not Affected by Confounding Factors FIG. 17 is a table showing results of correlation analysis between a patient's age and ELF and LEBS markers, according to one embodiment.

Given that the age and smoking history are the two major risk factors for pancreatic cancer, it was determined whether the changes in 4D-ELF and LEBS detect carcinogenesis rather than mere age difference and smoking history among patients with pancreatic cancer and control subjects. Thus, the variance of optical markers with patients' age and smoking history is determined. Two-way ANOVA analysis showed that none of the six markers changed significantly with either or age or smoking history, as shown in the figure. Therefore, the changes in the optical markers cannot be attributed to difference in age and smoking history in the patient population.

Further Applications of ELF and LEBS

The present invention also contemplates and includes additional applications of ELF and LEBS, including:

(1) Detection of early, previously undetectable stages of precancerous lesions in endoscopically or laparoscopically accessible organs, such as colon, esophagus, stomach, bladder, oral cavity, cervix, ovary, etc. This can be achieved by means of LEBS-guided colonoscopy.

(2) Screening or risk-stratification of patients for colorectal cancer (CRC) screening. As data indicate, LEBS and ELF has the potential to identify precancerous alterations in colon tissue far earlier than other currently known markers of colon carcinogenesis. If a colon tissue is accessed by means LEBS and ELF, only four readings would provide a 99% probability of correctly detecting abnormal signatures even at previously undetectable stages of carcinogenesis. Thus LEBS and ELF may be used to identify patients at increased risk of CRC and in the need of colonoscopy or treatment, such as chemoprevention. Not only does the combination of LEBS and ELF enable CRC detection at an early stage, it also enables the diagnosis of the presence of precancerous lesions (e.g. adenoma or carcinomas) by assessment of endoscopically and histologically normal-appearing tissue at a distance from a lesion. In particular, it has been demonstrated that LEBS and ELF assessment of rectal tissue alone (which can be easily accessed without the need for colonoscopy) reliably predicts the presence of adenoma or carcinomas anywhere else in the colon.

(3) Screening for pancreatic cancer. Pancreatic cancer is the fifth leading cause of cancer death in the United States with most cancers diagnosed at a late, incurable stage. Most of the existing approaches, including high-resolution imaging (MRI, CT, etc.), molecular diagnostics, and endoscopic cholangiopancreatography (ERCP), has not shown the capability to detect pancreatic neoplasms sufficiently early to allow effective treatment. Current imaging modalities as well as ERCP depend on the presence of a mass lesion, and, therefore, even if the resolution of these tests is improved, we will still be dealing with a tumor that is biologically too advanced for cure. Despite years of research no clinically adequate molecular markers have been developed. The only route that currently has the potential for diagnosing pre-invasive cancer is through the pancreatic duct, where 90% of adenocarcinomas of the pancreas originate. Due to the potential for complications including pancreatitis (3-5% cases), as currently performed, ERCP is not suitable for routine screening over successive points in time.

Given that the region around the ampulla of Vater is exposed to the same environmental and genetic milieu as the pancreatic duct, it is biologically plausible that the field effect should extend to this region of the small bowel. This opens up a possibility to diagnose pancreatic neoplasia by means of examination of duodenal and ampullar tissue in the vicinity of the pancreatic duct, which can be readily accomplished by means of existing upper-endoscopic techniques without the risk of pancreatitis or other serious complications.

A study has been initiated to explore the feasibility of detection of pancreatic neoplasms by means of spectroscopic assessment of a portion of duodenum and ampulla of Vater adjacent to the pancreatic duct and without the need to interrogate the pancreatic duct itself. The data involving 51 human subjects demonstrate that duodenal LEBS measurements enable detection of pancreatic early cancerous lesions (e.g. stage 1) with 96% sensitivity and 91% specificity.

(4) Monitoring of efficacy of chemoprevention and other anticancer strategies in humans. The ability to detect changes associated with the action of chemo-preventive agents is crucial for the development of effective anticancer strategies. A myriad of agents have demonstrated chemo-preventive efficacy in experimental systems. However, clinical studies remain difficult and expensive because of the insufficiency of existing intermediate biomarkers for early carcinogenesis and chemoprevention and, therefore, the long follow up needed to demonstrate the protective effects of agents. Thus, finding an easily detectable, sensitive, and accurate intermediate biomarker for colon carcinogenesis would be beneficial in designing chemo-preventive strategies. Ideally, such biomarker would quantitatively assess the efficacy of a chemo-preventive strategy early in the course of the therapy, which is of great benefit to patients undergoing the therapy, drug developers developing or evaluating the agent, and biomedical researchers investigating the mechanisms of carcinogenesis and chemoprevention. With unprecedented sensitivity and non-invasiveness, EBS may potentially become an ideal tool for monitoring of chemoprevention.

(5) Monitoring of efficacy of chemoprevention and other anticancer strategies in experimental models of CRC. Most cancer-prevention or treatment agents are first investigated in animal models, such as AOM-treated rat model discussed above. However, in this and similar models tumorigenesis is a long process. For example, in AOM-treated rat model, which is one of the most frequently used model of CRC, it takes more than 40 weeks for colon tumors to develop. This limits how fast the efficacy of a therapeutic or cancer-preventive agent can be tested in a pharmaceutical company or a research lab. As indicated by our results, LEBS may significantly decrease the time necessary to test experimental agents in animal models by sensing very early changes induced by the agent (within a few weeks instead of several months). This may potentially result in reduction of time necessary to develop and test anticancer agents.

(6) Monitoring bioengineered tissue during development, growth, and/or interaction with other tissues.

(7) Monitoring of the fabrication of elastomeric scaffolds, non-invasive measurement of the properties of the elastomeric scaffolds. For example, to assess the viability and the interaction with host tissue. A typical citric acid-based elastomer is poly(1,8 octanediol-co-citric acid) (POC). Another elastomer also under study is poly(glycerol sebacate) (PGS). LEBS can be used to characterize both POC and PGS elastomers as well as polystyrene of various molecular weights. As mechanical properties depend on the ultrastructure and chemical make up of a material, obtaining information pertinent to the degree of crosslinking (i.e. molecular weight between cross-links) should give insight into the mechanical properties of the material (i.e. Young's Modulus, tensile strength).

(8) Monitoring of the fabrication of polymers and non-invasive measurement of the properties of the polymers and the non-invasive measurements. For example, the slope of the intensity versus wavelength spectra wave can be determined to obtain correlation to mechanical and molecular weight data. The size distribution of the scattering structures can be correlated to mechanical and molecular weight data. There are intrinsic structural characteristics of polymers that can be correlated to the extent of reaction and mechanical properties. LEBS can detect morphological structures in solid polymeric materials which can be used to assess the extent of reaction and mechanical characteristics. The correlation between spectral slope and the log of molecular weight between cross links, Young's modulus and tensile strength, and the log of molecular weight can be determined.

(9) Assessment of various properties (e.g., size and granules) of the power materials such as dies.

(10) Monitoring the growth and development of human aortic smooth muscle cells. For example, the size distributions can be obtained from SMCs grown on laminin and fibornectin.

(11) Optical characterization of solid polymeric materials to determine the structural information. The combination of LEBS and ELF can be suitable for mechanical properties and molecular weight characterization of linear polymers.

Although embodiments have been described with reference to specific exemplary embodiments, it will be evident that the various modification and changes can be made to these embodiments. Accordingly, the specification and drawings are to be regarded in an illustrative sense rather than in a restrictive sense. The foregoing specification provides a description with reference to specific exemplary embodiments. It will be evident that various modifications may be made thereto without departing from the broader spirit and scope as set forth in the following claims. The specification and drawings are, accordingly, to be regarded in an illustrative sense rather than a restrictive sense.

What is claimed is:

1. A method for measuring the properties of a target object, comprising the steps of:
    recording an intensity of one or more of at least one spectral component and at least one angular component of backscattered light, wherein the backscattered light is to be backscattered from the illumination of incident light on a target object;
    selecting a depth of penetration of the target object by the incident light via adjusting a spatial coherence length of the incident light, wherein the depth of penetration is to be determined as based upon characteristics of the target object; and
    further recording an intensity of at least one azimuth angle of the one or more of at least one spectral component and the at least one angular component of the backscattered light, wherein the angular component of the backscattered light is an angle between the backscattered light propagation direction and the incident light propagation direction, and the azimuth angle is an angle between the incident light polarization and the projection of the direction of the incident light onto a plane in which an electric field of the incident light oscillates.

2. The method of claim 1, further comprising recording an intensity of at least one polarization of the one or more of the at least one spectral component and the at least one angular component of the backscattered light, wherein the at least one polarization is co-polarized or cross-polarized to the incident light polarization, wherein co-polarized backscattered light is substantially parallel to the incident light polarization and cross-polarized backscattered light is substantially perpendicular to the incident light polarization.

3. The method of claim 2, wherein the substantially parallel is parallel to the incident light polarization.

4. The method of claim 2, wherein the substantially parallel is at one of a greater and smaller angle than a direction parallel to the incident light polarization.

5. The method of claim 2, wherein the substantially perpendicular is perpendicular to the incident light polarization.

6. The method of claim 2, wherein the substantially perpendicular is at one of a greater and smaller angle than a direction perpendicular to the incident light polarization.

7. The method of claim 1, further comprising analyzing the intensity of the one or more of the at least one spectral component and the at least one angular component of the backscattering angle of backscattered light to obtain a first set of optical markers of the backscattered light, toward evaluating said properties.

8. The method of claim 1, wherein the backscattered light is low coherence enhanced backscattered light.

9. The method of claim 7, wherein the first set of optical markers comprises at least one of a spectral marker and an angular marker.

10. The method of claim 9, wherein the angular marker is a decay rate of a Fourier transform of the intensity of the at least one angular component of the backscattered light with respect to an independent Fourier variable of the Fourier transform.

11. The method of claim 9, wherein the angular marker is a correlation decay rate of the intensity of the at least one angular component of the backscattered light.

12. The method of claim 9, wherein the angular marker is at least one of an angular width and enhancement factor of the intensity of the at least one angular component of the backscattered light.

13. The method of claim 9, wherein the spectral marker is one or more of a spectral slope, a correlation decay rate, and at least one principal component of the intensity of the at least one spectral component of the backscattered light.

14. The method of claim 9, wherein the spectral marker is a spectral exponential of the at least one spectral component of the backscattered light.

15. The method of claim 1, further comprising analyzing the intensity of the at least one azimuth angle of the one or more of the at least one spectral component and the at least one angular component of the backscattered light to obtain one or more of a second set of optical markers of the backscattered light, toward evaluating said properties.

16. The method of claim 15, further comprising obtaining one or more of the second set of optical markers of the backscattered light via analyzing the intensity of the at least one polarization of the at least one spectral component and the at least one angular component of the backscattered light.

17. The method of claim 16, wherein the analyzing the intensity of the at least one polarization comprises: obtaining a differential polarization signal, wherein the differential polarization signal is a difference in an intensity of the co-polarized backscattered light and the cross-polarized backscattered light.

18. The method of claim 15, wherein the second set of optical markers comprises at least one of a spectral marker and an angular marker.

19. The method of claim 18, wherein the angular marker is a decay rate of a Fourier transform of the intensity of the at least one angular component of the backscattered light with respect to an independent Fourier variable of the Fourier transform.

20. The method of claim 18, wherein the angular marker is a correlation decay rate of the intensity of the at least one angular component of the backscattered light.

21. The method of claim 18, wherein the angular marker is at least one of an angular width and enhancement factor of the intensity of the at least one angular component of the backscattered light.

22. The method of claim 18, wherein the spectral marker is one or more of a spectral slope, a correlation decay rate, a fractal dimension, and at least one principal component of the intensity of the at least one spectral component of the backscattered light.

23. The method of claim 18, wherein the spectral marker is a spectral exponential of the at least one spectral component of the backscattered light.

24. The method of claim 1, further comprising providing the incident light to be illuminated on the target object, wherein the incident light comprises at least one spectral component having low coherence.

25. The method of claim 1, wherein the incident light is to be projected onto the target having an angle of incidence greater than zero degrees to mitigate specular reflection from the target, wherein the angle of incidence is the angle between the incident light propagation direction and a direction normal to the target.

26. The method of claim 1, further comprising collecting at least one spectral component of the backscattered light to detect backscattered light having low temporal coherence length.

27. The method of claim 1, wherein the recording comprises simultaneous measurement of the at least one spectral component and the at least one angular component of the backscattered light.

28. The method of claim 27, wherein the recording comprises recording a matrix of intensities of backscattered light as a function of wavelength and backscattering angle.

29. The method of claim 1, wherein the depth of penetration is substantially the spatial coherence length of the incident light.

30. The method of claim 1, further comprising determining the depth of penetration of the incident light based on at least one angular component of the backscattered light.

31. The method of claim 30, wherein a large angular component of the backscattered light corresponds to a small depth of penetration of the incident light and a small angular component of the backscattered light corresponds to a large depth of penetration of the incident light.

32. The method of claim 1, further comprising determining the depth of penetration of the target by the incident light based on a probability of radial distribution intensity of the backscattered light.

33. The method of claim 1, wherein the target object is at least a portion of the living subject.

34. The method of claim 33, wherein the sample is a biological sample.

35. The method of claim 34, wherein the biological sample comprises tissue undergoing neoplastic transformation.

36. The method of claim 35, wherein the neoplastic transformation is cancer.

37. The method of claim 36, wherein the cancer is at least one of a pancreatic cancer, colon cancer, liver cancer, lung cancer, esophageal cancer, stomach cancer, cervical cancer, oral cavity cancer, ovarian cancer, breast cancer, bladder cancer, cholangiocarcinoma, prostate cancer, and head and neck cancer.

38. The method of claim 1, wherein the target object is illuminated in vivo.

39. The method of claim 1, further comprising acquiring an image of the target object.

40. The method of claim 1, further comprising identifying the depth of penetration of the target object by the incident light where the optical marker of the backscattered light is sensitive to biological changes of the target object.

41. The method of claim 40, further comprising obtaining the optical marker from non-neoplastic tissue to detect one or more of adenoma and carcinoma of tissue obtained from a different anatomic portion than the non-neoplastic tissue.

42. The method of claim 41, further comprising obtaining the optical marker from tissue of an anatomical region at least one of a proximal and distal to tissue of the anatomical region potentially harboring one or more of adenoma and carcinoma.

43. The method of claim 42, further comprising detecting presence of one or more of adenoma and carcinoma in at least a part of the colon via detecting optical changes via at least one optical marker from tissue obtained from anywhere in the colon.

44. The method of claim 43, the tissue to be obtained from the anywhere in the colon comprises at least one of a cecum, ascending colon, hepatic flexure, transverse colon, splenic flexure, descending colon, sigmoid colon, and rectum.

45. The method of claim 44, wherein the tissue is one or more of an endoscopically normal tissue and a histologically normal tissue.

46. The method of claim 41, further comprising detecting pancreatic neoplasia via detecting optical changes via at least one of the first set and the second set of optical markers obtained from non-neoplastic tissue.

47. The method of claim 46, wherein the non-neoplastic tissue is duodenal periampullary mucosa.

48. The method of claim 46, wherein the non-neoplastic tissue is any tissue affected by at least one of a genetic and environmental milieu to result in the pancreatic neoplasia.

49. The method of claim 48, wherein the non-neoplastic tissue is one or more of an endoscopically normal tissue and a histologically normal tissue.

50. The method of claim 1, further comprising acquiring an image of the target object.

51. The method of claim 1, wherein the target object comprises a polymer.

52. The method of claim 51, wherein the polymer is a translucent crosslinked polymer.

53. The method of claim 51, wherein the polymer is a citric acid-based elastomer.

54. The method of claim 51, wherein the polymer is one or more of poly(1,8 octanediol-co-citric acid) and poly(glycerol sebacate).

55. A system to measure the properties of a target object, comprising:
 means for recording an intensity of one or more of at least one spectral component and at least one angular component of the backscattered light, wherein the backscattered light is to be backscattered from the illumination of incident light on a target object;
 a means for selecting a depth of penetration of the target object by the incident light via adjusting a spatial coherence length of the incident light, wherein the depth of penetration is to be determined based on characteristics of the target object; and
 a means for further recording an intensity of at least one azimuth angle of the one or more of at least one spectral component and the at least one angular component of the backscattered light, wherein the angular component of the backscattered light is an angle between the backscattered light propagation direction and the incident light propagation direction, and the azimuth angle is an angle between the incident light polarization and the projection of the direction of the incident light onto a plane in which electric field of the incident light oscillates.

56. A method for measuring the properties of a target object, comprising:
 recording an intensity of one or more of at least one spectral component and at least one angular component of backscattered light, wherein the backscattered light is to be backscattered from the illumination of incident light on a target object in vivo;
 selecting a depth of penetration of the target object by the incident light, via adjusting a spatial coherence length of the incident light, wherein the depth of penetration is to be determined based upon characteristics of the target object; and
 further recording an intensity of at least one azimuth angle of the one or more of at least one spectral component and the at least one angular component of the backscattered light, wherein the angular component of the backscattered light is an angle between the backscattered light propagation direction and the incident light propagation direction, and the azimuth angle is an angle between incident light polarization and a projection of the direction of the backscattered light propagation onto a plane in which the incident electric field oscillates.

* * * * *

UNITED STATES PATENT AND TRADEMARK OFFICE
CERTIFICATE OF CORRECTION

PATENT NO. : 8,131,348 B2
APPLICATION NO. : 11/803418
DATED : March 6, 2012
INVENTOR(S) : Vadim Backman et al.

It is certified that error appears in the above-identified patent and that said Letters Patent is hereby corrected as shown below:

Title page, Item (75), third named inventor, change "Brand Randall" --to-- "Randall Brand".

Signed and Sealed this
Twenty-ninth Day of May, 2012

David J. Kappos
*Director of the United States Patent and Trademark Office*